(12) United States Patent
Moskowitz et al.

(10) Patent No.: US 9,848,993 B2
(45) Date of Patent: Dec. 26, 2017

(54) ZERO-PROFILE EXPANDABLE INTERVERTEBRAL SPACER DEVICES FOR DISTRACTION AND SPINAL FUSION AND A UNIVERSAL TOOL FOR THEIR PLACEMENT AND EXPANSION

(71) Applicants: Ahmnon D. Moskowitz, Rockville, MD (US); Mosheh T. Moskowitz, Rockville, MD (US); Pablo A. Valdivia Y. Alvarado, Cambridge, MA (US); Eric Sugalski, Arlington, MA (US); Nathan C. Moskowitz, Rockville, MD (US)

(72) Inventors: Ahmnon D. Moskowitz, Rockville, MD (US); Mosheh T. Moskowitz, Rockville, MD (US); Pablo A. Valdivia Y. Alvarado, Cambridge, MA (US); Eric Sugalski, Arlington, MA (US); Nathan C. Moskowitz, Rockville, MD (US)

(73) Assignee: Nathan C. Moskowitz, Rockville, MD (US)

(*) Notice: Subject to any disclaimer, the term of this patent is extended or adjusted under 35 U.S.C. 154(b) by 0 days.

(21) Appl. No.: 14/063,197

(22) Filed: Oct. 25, 2013

(65) Prior Publication Data
US 2014/0249629 A1    Sep. 4, 2014

Related U.S. Application Data

(60) Continuation-in-part of application No. 13/210,150, filed on Aug. 15, 2011, which is a continuation of
(Continued)

(51) Int. Cl.
*A61F 2/44*        (2006.01)
*A61B 17/064*    (2006.01)
(Continued)

(52) U.S. Cl.
CPC .......... *A61F 2/447* (2013.01); *A61B 17/0642* (2013.01); *A61B 17/7064* (2013.01);
(Continued)

(58) Field of Classification Search
CPC . A61B 17/0642; A61B 17/7064; A61B 17/86; A61B 2017/922; A61B 17/8875;
(Continued)

(56) References Cited

U.S. PATENT DOCUMENTS 2,360,942 A    10/1944   Ellerstein
4,064,881 A    12/1977   Meredith
(Continued)

FOREIGN PATENT DOCUMENTS

FR        2727003        5/1996
WO    2004/093749    11/2004
(Continued)

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Pedro Philogene
(74) *Attorney, Agent, or Firm* — Fish & Richardson P.C.

(57) ABSTRACT

A unique, universal Zero-Profile Expandable Intervertebral Spacer (ZP-EIS) device for fusion and distraction throughout the entire spine is provided which can be inserted via anterior, anterolateral, lateral, far lateral or posterior surgical approaches dependent on the need and preference. Multiple ZP-EIS embodiments each with unique mechanisms of calibrated expansion are provided. Two of these embodiments incorporate bi-directional fixating transvertebral (BDFT) screws and five other embodiments do not incor-
(Continued)

porate BDFT screws. A tool for implantation into the intervertebral device and calibrated device expansion is also disclosed.

55 Claims, 38 Drawing Sheets

Related U.S. Application Data application No. 13/084,543, filed on Apr. 11, 2011, now Pat. No. 8,353,913, and a continuation of application No. 13/108,982, filed on May 16, 2011, said application No. 13/084,543 is a division of application No. 11/842,855, filed on Aug. 21, 2007, now Pat. No. 7,942,903, said application No. 13/108,982 is a continuation of application No. 11/842,855, filed on Aug. 21, 2007, now Pat. No. 7,942,903, said application No. 13/084,543 is a division of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 14/063,197, which is a continuation-in-part of application No. 13/210,157, filed on Aug. 15, 2011, which is a continuation of application No. 13/084,543, filed on Apr. 11, 2011, now Pat. No. 8,353,913, and a continuation of application No. 13/108,982, filed on May 16, 2011, said application No. 13/084,543 is a division of application No. 11/842,855, filed on Aug. 21, 2007, now Pat. No. 7,942,903, said No. 13/108,982 is a continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 14/063,197, which is a continuation-in-part of application No. 13/210,162, filed on Aug. 15, 2011, which is a continuation of application No. 13/084,543, filed on Apr. 11, 2011, now Pat. No. 8,353,913, and a continuation of application No. 13/108,982, filed on May 16, 2011, said application No. 13/084,543 is a division of application No. 11/842,855, filed on Aug. 21, 2007, now Pat. No. 7,942,903, said No. 13/108, 982 is a continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 14/063,197, which is a continuation-in-part of application No. 13/210,168, filed on Aug. 15, 2011, and a continuation-in-part of application No. 13/741,361, filed on Jan. 14, 2013, now Pat. No. 9,301,854, which is a continuation of application No. 13/084,543, filed on Apr. 11, 2011, now Pat. No. 8,353,913, and a continuation of application No. 13/108,982, filed on May 16, 2011, now Pat. No. 9,005,293, said application No. 13/084,543 is a division of application No. 11/842,855, filed on Aug. 21, 2007, now Pat. No. 7,942,903, said application No. 13/108,982 is a continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, said application No. 13/210,168 is a continuation of application No. 13/084,543, filed on Apr. 11, 2011, now Pat. No. 8,353,913, and a continuation of application No. 13/108,982, filed on May 16, 2011, now Pat. No. 9,005,293, said application No. 13/108,982 is a continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005, provisional application No. 61/801,783, filed on Mar. 15, 2013, provisional application No. 61/718,707, filed on Oct. 25, 2012.

(51) Int. Cl.
    *A61F 2/46*     (2006.01)
    *A61B 17/70*     (2006.01)
    *A61B 17/86*     (2006.01)
    *A61B 17/92*     (2006.01)
    *A61F 2/28*     (2006.01)
    *A61F 2/30*     (2006.01)
    *A61B 17/88*     (2006.01)
    *A61B 17/02*     (2006.01)

(52) U.S. Cl.
CPC ............. *A61F 2/4611* (2013.01); *A61B 17/86* (2013.01); *A61B 17/8875* (2013.01); *A61B 2017/0256* (2013.01); *A61B 2017/922* (2013.01); *A61F 2002/2835* (2013.01); *A61F 2002/3055* (2013.01); *A61F 2002/30261* (2013.01); *A61F 2002/30266* (2013.01); *A61F 2002/30281* (2013.01); *A61F 2002/30387* (2013.01); *A61F 2002/30448* (2013.01); *A61F 2002/30471* (2013.01); *A61F 2002/30497* (2013.01); *A61F 2002/30507* (2013.01); *A61F 2002/30525* (2013.01); *A61F 2002/30538* (2013.01); *A61F 2002/30556* (2013.01); *A61F 2002/30579* (2013.01); *A61F 2002/30604* (2013.01); *A61F 2002/30772* (2013.01); *A61F 2002/30878* (2013.01); *A61F 2002/448* (2013.01); *A61F 2002/4475* (2013.01); *A61F 2002/4627* (2013.01); *A61F 2002/4681* (2013.01); *A61F 2002/4687* (2013.01); *A61F 2220/005* (2013.01); *A61F 2220/0025* (2013.01); *A61F 2230/0015* (2013.01); *A61F 2250/0007* (2013.01)

(58) Field of Classification Search
CPC ............. A61B 2017/0256; A61F 2/447; A61F 2/4611; A61F 2002/30556; A61F 2002/2835; A61F 2002/30387; A61F 2002/30448; A61F 2002/30507; A61F 2002/3055; A61F 2002/30579; A61F 2002/30604; A61F 2002/30772; A61F 2002/30878; A61F 2002/4475; A61F 2002/448; A61F 2002/4627; A61F 2002/4681; A61F 2002/30266; A61F 2002/30281; A61F 2002/30471; A61F 2002/30538; A61F 2220/0025; A61F 2220/005; A61F 2250/0007; A61F 2230/0015

USPC .................................. 606/246–279, 301, 99

See application file for complete search history.

(56) References Cited

U.S. PATENT DOCUMENTS

| | | | |
|---|---|---|---|
| 4,554,914 A | 11/1985 | Kapp et al. | |
| 4,599,086 A | 7/1986 | Doty | |
| 4,636,217 A * | 1/1987 | Ogilvie | A61F 2/44 606/247 |
| 4,904,261 A | 2/1990 | Dove et al. | |
| 4,960,420 A | 10/1990 | Goble et al. | |
| 4,997,432 A | 3/1991 | Keller | |
| 5,005,749 A | 4/1991 | Aranyi | |
| 5,062,850 A | 11/1991 | MacMillan et al. | |
| 5,123,926 A | 6/1992 | Pisharodi | |
| 5,290,312 A * | 3/1994 | Kojimoto | A61F 2/44 606/247 |
| 5,405,391 A | 4/1995 | Hednerson et al. | |
| 5,413,583 A | 5/1995 | Wohlers | |
| 5,454,819 A | 10/1995 | Knoepfler | |
| 5,514,180 A | 5/1996 | Heggeness et al. | |
| 5,660,188 A | 8/1997 | Groiso | |
| 5,667,472 A | 9/1997 | Finn et al. | |
| 5,713,912 A | 2/1998 | Porter | |
| 5,782,832 A | 7/1998 | Larsen et al. | |
| 5,865,848 A | 2/1999 | Baker | |
| 5,888,223 A | 3/1999 | Bray, Jr. | |
| 5,916,224 A | 6/1999 | Esplin | |
| 5,951,574 A | 9/1999 | Stefanchik et al. | |
| 5,960,522 A | 10/1999 | Boe | |
| 5,968,054 A | 10/1999 | Yeatts et al. | |
| 5,976,136 A | 11/1999 | Bailey et al. | |
| 6,126,689 A | 10/2000 | Brett | |
| 6,224,602 B1 | 5/2001 | Hayes | |
| 6,235,034 B1 | 5/2001 | Bray | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 | 8/2002 | Fraser | |
| 6,454,807 B1 * | 9/2002 | Jackson | A61F 2/447 623/17.15 |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,558,423 B1 | 5/2003 | Michelson | |
| 6,572,653 B1 | 6/2003 | Simonson | |
| 6,579,318 B2 | 6/2003 | Varga et al. | |
| 6,582,468 B1 | 6/2003 | Gauchet | |
| 6,613,055 B2 | 9/2003 | Di Emidio | |
| 6,629,998 B1 | 10/2003 | Lin | |
| 6,641,614 B1 | 11/2003 | Wagner et al. | |
| 6,655,243 B2 | 12/2003 | Anderson et al. | |
| 6,716,247 B2 | 4/2004 | Michelson | |
| 6,719,794 B2 | 4/2004 | Gerber | |
| 6,723,126 B1 * | 4/2004 | Berry | A61F 2/4611 606/247 |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,824,564 B2 | 11/2004 | Crozet | |
| 6,852,117 B2 | 2/2005 | Orlowski | |
| 6,890,355 B2 | 5/2005 | Michelson | |
| 6,904,308 B2 | 6/2005 | Frisch et al. | |
| 6,953,477 B2 | 10/2005 | Berry | |
| 6,955,671 B2 | 10/2005 | Uchikubo | |
| 6,962,606 B2 | 11/2005 | Michelson | |
| 6,972,019 B2 | 12/2005 | Michelson | |
| 6,974,480 B2 | 12/2005 | Messerli et al. | |
| 7,030,904 B2 | 4/2006 | Adair et al. | |
| 7,033,394 B2 | 4/2006 | Michelson | |
| 7,037,258 B2 | 5/2006 | Chatenever et al. | |
| 7,077,864 B2 | 7/2006 | Byrd et al. | |
| 7,097,615 B2 | 8/2006 | Banik et al. | |
| 7,135,043 B2 | 11/2006 | Nakahara et al. | |
| 7,211,112 B2 * | 5/2007 | Baynham | A61F 2/447 623/17.11 |
| 7,232,464 B2 | 6/2007 | Mathieu et al. | |
| 7,238,203 B2 | 7/2007 | Bagga et al. | |
| 7,326,248 B2 | 2/2008 | Michelson | |
| 7,442,209 B2 | 10/2008 | Michelson | |
| 7,442,299 B2 | 10/2008 | Lee et al. | |
| 7,615,059 B2 | 11/2009 | Watschke et al. | |
| 7,618,456 B2 | 11/2009 | Mathieu et al. | |
| 7,628,816 B2 | 12/2009 | Magerl et al. | |
| 7,704,279 B2 | 4/2010 | Moskowitz et al. | |
| 7,727,246 B2 | 6/2010 | Sixto et al. | |
| 7,776,047 B2 | 8/2010 | Fanger et al. | |
| 7,776,093 B2 | 8/2010 | Wolek et al. | |
| 7,799,081 B2 * | 9/2010 | McKinley | A61F 2/4455 623/17.16 |
| 7,803,162 B2 | 9/2010 | Marnay et al. | |
| 7,846,207 B2 | 12/2010 | Lechmann et al. | |
| 7,850,733 B2 * | 12/2010 | Baynham | A61F 2/447 623/17.11 |
| 7,862,616 B2 | 1/2011 | Lechmann et al. | |
| 7,875,076 B2 | 1/2011 | Mathieu et al. | |
| 7,887,591 B2 | 2/2011 | Aebi et al. | |
| 7,942,903 B2 | 5/2011 | Moskowitz et al. | |
| 7,959,675 B2 | 6/2011 | Gately | |
| 7,972,363 B2 | 7/2011 | Moskowitz et al. | |
| 7,985,255 B2 | 7/2011 | Bray et al. | |
| 8,029,512 B2 | 10/2011 | Paltzer | |
| 8,034,060 B2 | 10/2011 | Keren et al. | |
| 8,105,367 B2 | 1/2012 | Austin et al. | |
| 8,114,162 B1 | 2/2012 | Bradley | |
| 8,137,405 B2 | 3/2012 | Kostuik et al. | |
| 8,167,949 B2 | 5/2012 | Tyber et al. | |
| 8,268,000 B2 | 9/2012 | Waugh et al. | |
| 8,273,127 B2 | 9/2012 | Jones et al. | |
| 8,328,872 B2 | 12/2012 | Duffield et al. | |
| 8,353,913 B2 | 1/2013 | Moskowitz et al. | |
| 8,403,986 B2 | 3/2013 | Michelson | |
| 8,414,651 B2 | 4/2013 | Tyber et al. | |
| 8,419,797 B2 | 4/2013 | Biedermann et al. | |
| 8,425,607 B2 | 4/2013 | Waugh et al. | |
| 8,535,380 B2 * | 9/2013 | Greenhalgh | A61B 17/8858 606/90 |
| 8,540,774 B2 | 9/2013 | Kueenzi et al. | |
| 8,613,761 B2 | 12/2013 | Lindemann et al. | |
| 8,728,165 B2 | 5/2014 | Parry et al. | |
| 8,790,405 B2 | 7/2014 | Biedermann et al. | |
| 2002/0068977 A1 | 6/2002 | Jackson | |
| 2002/0143338 A1 | 10/2002 | Orbay et al. | |
| 2003/0130737 A1 | 7/2003 | McGahan et al. | |
| 2004/0088054 A1 | 5/2004 | Berry | |
| 2004/0177531 A1 | 9/2004 | DiBenedetto et al. | |
| 2004/0186569 A1 | 9/2004 | Berry | |
| 2004/0193272 A1 | 9/2004 | Zubok et al. | |
| 2004/0220571 A1 | 11/2004 | Assaker et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0256576 A1 | 11/2005 | Moskowitz et al. | |
| 2005/0261769 A1 | 11/2005 | Moskowitz et al. | |
| 2005/0273170 A1 | 12/2005 | Navarro et al. | |
| 2005/0278026 A1 | 12/2005 | Gordon et al. | |
| 2006/0155285 A1 | 7/2006 | Anderson | |
| 2006/0241621 A1 | 10/2006 | Moskowitz et al. | |
| 2007/0049943 A1 | 3/2007 | Moskowitz et al. | |
| 2007/0167678 A1 | 7/2007 | Moskowitz et al. | |
| 2007/0198089 A1 | 8/2007 | Moskowitz et al. | |
| 2007/0213820 A1 | 9/2007 | Magerl et al. | |
| 2007/0250167 A1 | 10/2007 | Bray et al. | |
| 2007/0250172 A1 | 10/2007 | Moskowitz et al. | |
| 2007/0276498 A1 | 11/2007 | Aebi et al. | |
| 2008/0033440 A1 | 2/2008 | Moskowitz et al. | |
| 2008/0177307 A1 | 7/2008 | Moskowitz et al. | |
| 2008/0183293 A1 | 7/2008 | Parry et al. | |

(56) References Cited

U.S. PATENT DOCUMENTS

| | | |
|---|---|---|
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0281424 A1 | 11/2008 | Parry et al. |
| 2008/0281425 A1 | 11/2008 | Thalgott et al. |
| 2009/0030520 A1 | 1/2009 | Biedermann et al. |
| 2009/0080997 A1 | 3/2009 | Johnson |
| 2009/0105830 A1 | 4/2009 | Jones et al. |
| 2009/0105831 A1 | 4/2009 | Jones et al. |
| 2009/0112271 A1 | 4/2009 | Moskowitz et al. |
| 2009/0182430 A1 | 7/2009 | Tyber et al. |
| 2009/0187218 A1 | 7/2009 | Schaffhausen |
| 2009/0210062 A1 | 8/2009 | Thalgott et al. |
| 2009/0224023 A1 | 9/2009 | Moskowitz et al. |
| 2009/0234455 A1 | 9/2009 | Moskowitz et al. |
| 2010/0145460 A1 | 6/2010 | McDonough et al. |
| 2010/0305704 A1 | 12/2010 | Messerli et al. |
| 2010/0324606 A1 | 12/2010 | Moskowitz et al. |
| 2011/0125269 A1 | 5/2011 | Moskowitz et al. |
| 2011/0137349 A1 | 6/2011 | Moskowitz et al. |
| 2011/0178600 A1 | 7/2011 | Moskowitz et al. |
| 2011/0208312 A1 | 8/2011 | Moskowitz et al. |
| 2011/0288646 A1 | 11/2011 | Moskowitz et al. |
| 2011/0295327 A1 | 12/2011 | Moskowitz et al. |
| 2011/0295371 A1 | 12/2011 | Moskowitz et al. |
| 2011/0307011 A1 | 12/2011 | Moskowitz et al. |
| 2011/0319935 A1 | 12/2011 | Moskowitz et al. |
| 2012/0010714 A1 | 1/2012 | Moskowitz et al. |
| 2012/0271423 A1 | 10/2012 | Wallenstein et al. |
| 2012/0277870 A1 | 11/2012 | Wolters et al. |
| 2012/0323330 A1 | 12/2012 | Kueenzi et al. |
| 2012/0330419 A1 | 12/2012 | Moskowitz et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0060339 A1 | 3/2013 | Duffield et al. |
| 2013/0073044 A1 | 3/2013 | Gamache |
| 2013/0173002 A1 | 7/2013 | Moskowitz et al. |
| 2013/0282017 A1 | 10/2013 | Moskowitz et al. |
| 2015/0025637 A1 | 1/2015 | Moskowitz et al. |
| 2015/0105824 A1 | 4/2015 | Moskowitz et al. |
| 2015/0148847 A1 | 5/2015 | Moskowitz et al. |
| 2016/0374830 A1 | 12/2016 | Moskowitz et al. |
| 2017/0252178 A1 | 9/2017 | Moskowitz et al. |

FOREIGN PATENT DOCUMENTS

| | | |
|---|---|---|
| WO | 2004093749 A1 | 11/2004 |
| WO | 2006/091503 | 8/2006 |
| WO | 2006091503 A1 | 8/2006 |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. to Aug. 1, 2003, pp. S15-S23.

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, Dec. 3, 2007, International Application No. PCT/US 07/05005.

International Search Report (ISR) and Written Opinion of the International Searching Authority, May 21, 2008, International Application No. PCT/US2007/021015.

International Search Report (ISR) and Written Opinion of the International Searching Authority, Jul. 9, 2008, International Application No. PCT/US2007021013.

* cited by examiner

500

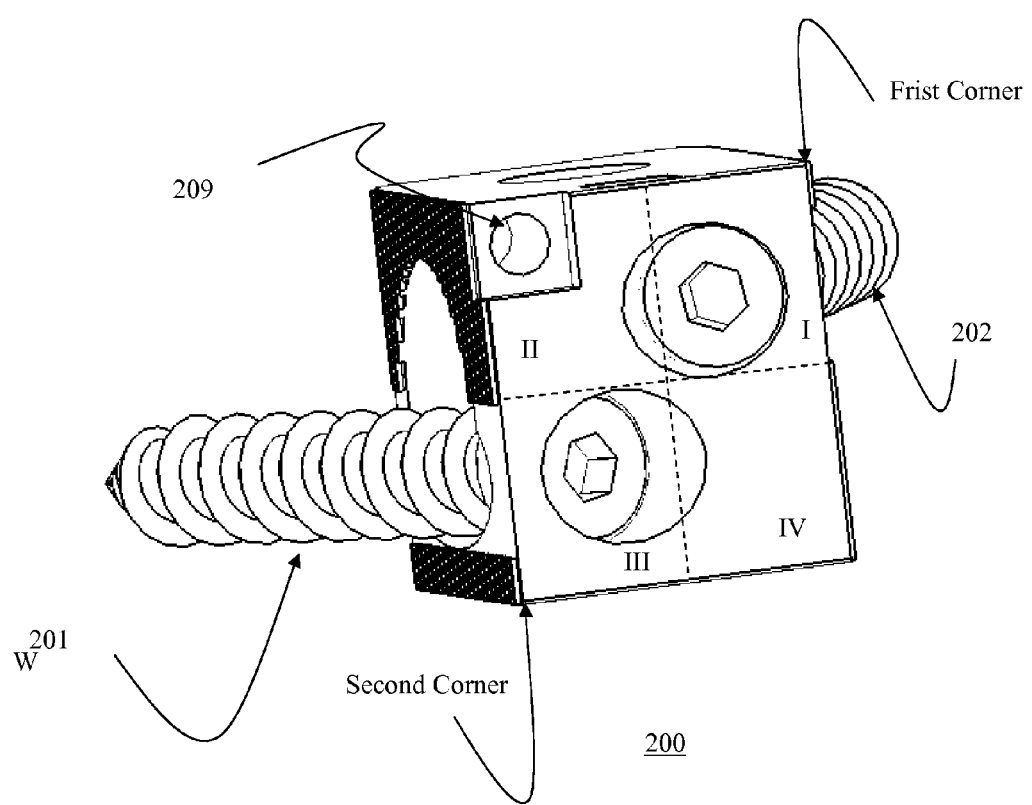
Fig. 7E(ii)

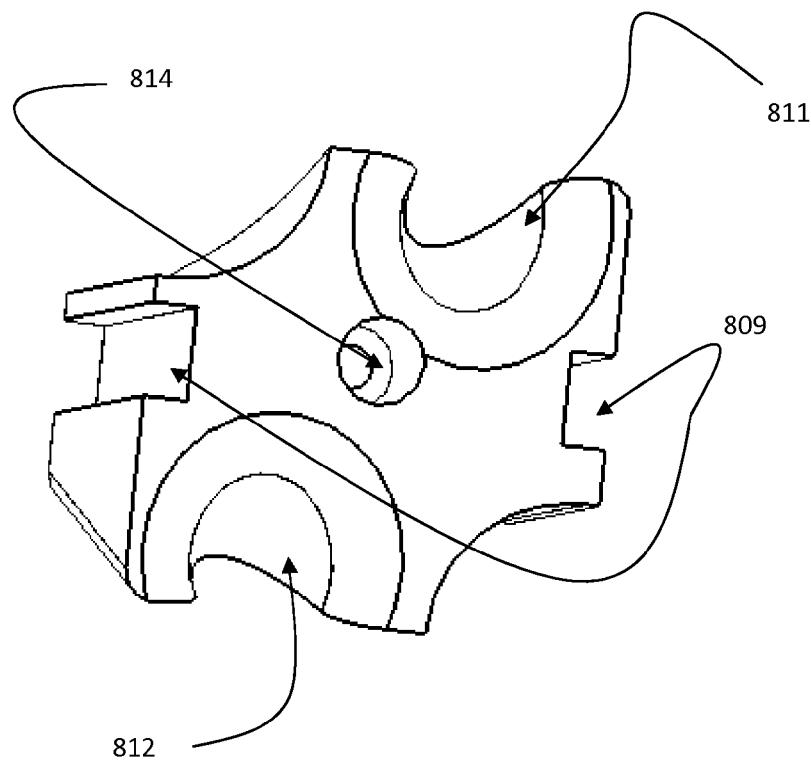
Fig. 8D(i)
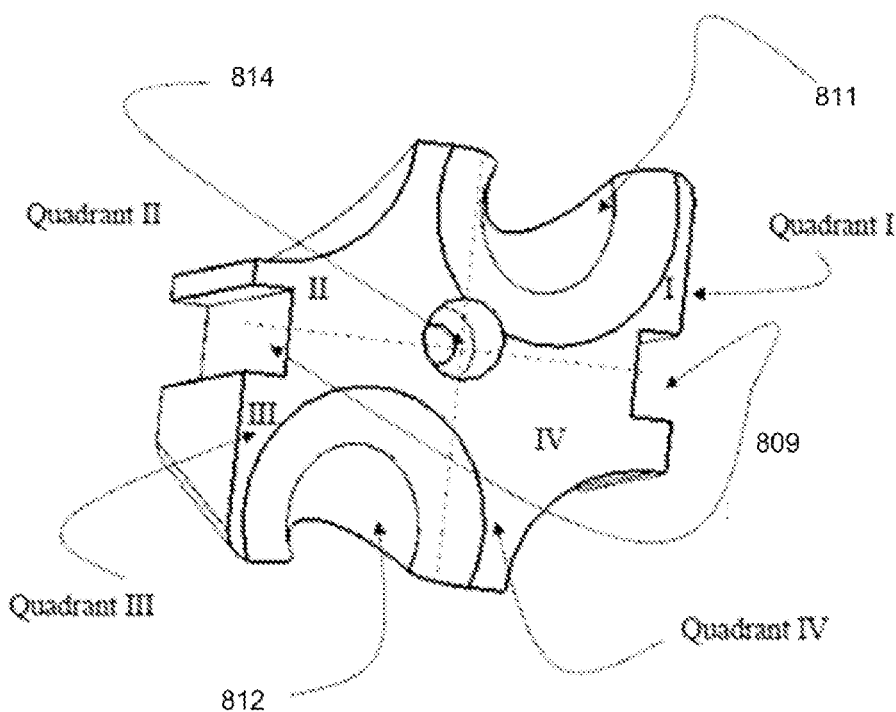
Fig. 8D(ii)

ZERO-PROFILE EXPANDABLE INTERVERTEBRAL SPACER DEVICES FOR DISTRACTION AND SPINAL FUSION AND A UNIVERSAL TOOL FOR THEIR PLACEMENT AND EXPANSION

CROSS-REFERENCE TO RELATED APPLICATIONS

This application is a Continuation-in-part Application of each of co-pending application Ser. No. 13/210,150, filed on Aug. 15, 2011, co-pending application Ser. No. 13/210,157, filed on Aug. 15, 2011, co-pending application Ser. No. 13/210,162, filed on Aug. 15, 2011, co-pending application Ser. No. 13/210,168, filed on Aug. 15, 2011, co-pending application Ser. No. 13/741,361, filed on Jan. 14, 2013, each of which is a Continuation Application of application Ser. No. 13,084,543, filed on Apr. 11, 2011, now U.S. Pat. No. 8,353,913 issued on Jan. 15, 2013, which is a Divisional Application of application Ser. No. 11/842,855, filed on Aug. 21, 2007, now U.S. Pat. No. 7,942,903 issued on May 17, 2011, and a Continuation Application of application Ser. No. 13,108,982, filed on May 16, 2011, which also is a Continuation Application of application Ser. No. 11/842, 855, filed on Aug. 21, 2007, now U.S. Pat. No. 7,942,903 issued on May 17, 2011, which is a Continuation-In-Part Application of application Ser. No. 11/536,815, filed on Sep. 29, 2006, now U.S. Pat. No. 7,846,188 issued on Dec. 7, 2010, which is a Continuation-In-Part Application of application Ser. No. 11/208,644, filed on Aug. 23, 2005, now U.S. Pat. No. 7,704,279 issued on Apr. 27, 2010, for which priority is claimed under 35 U.S.C. §120; and this application also claims priority under 35 U.S.C. §119(e) of U.S. provisional application No. 61/801,783, filed on Mar. 15, 2013, U.S. provisional application No. 61/718,707, filed on Oct. 25, 2012, and U.S. provisional application No. 60/670, 231, filed on Apr. 12, 2005; the entire contents of all the above identified patent applications are hereby incorporated by reference.

U.S. patent application Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, each claim the benefit of priority under 35 U.S.C. §119(e) of U.S. Provisional Application No. 60/670,231, filed on Apr. 12, 2005, and this application hereby incorporates the claim of priority to this provisional application under 35 U.S.C. §119(e) from the aforementioned intermediate applications (for which priority of each intermediate application is claimed under 35 U.S.C. §120); and the entire contents of all of the above identified patent applications are hereby incorporated by reference in their entirety.

FIELD OF DISCLOSURE

The present invention relates to unique, universal Zero-Profile Expandable Intervertebral Spacer (ZP-EIS) devices for fusion and distraction throughout the entire spine which can be inserted via anterior, anterolateral, lateral, far lateral or posterior surgical approaches dependent on the need and preference. Multiple ZP-EIS embodiments each with unique mechanisms of calibrated expansion are presented. Two of these embodiments incorporate bi-directional fixating transvertebral (BDFT) screws and five other embodiments do not incorporate BDFT screws. A universal tool for their intervertebral placement and device expansion is also described.

The ZP-EIS embodiments with incorporated BDFT screws can be used as stand-alone intervertebral devices. These exemplary embodiments combine the dual functions of intervertebral calibrated expandable distraction, and segmental vertebral body spinal fusion. These embodiments can include bone cavities which can be filled with bone fusion material(s) to promote segmental spinal fusion.

The calibrated ZP-EIS embodiments without incorporated BDFT screws can also be used as stand-alone devices for calibrated intervertebral expansion and segmental vertebral body fusion. The exemplary devices can include bone cavities which can be filled with bone fusion material. If desirable, the exemplary devices can be supplemented with other forms of screw stabilization.

The exemplary ZP-EIS embodiments, especially those with incorporated BDFT screws, may obviate the need for supplemental pedicle screw fixation in many situations. The exemplary embodiments allow nuanced, fine-tuned incremental and calibrated distraction of the disc space to allow nerve root decompression in a minimally invasive and safe manner, as well as promoting segmental spinal fusion.

In the related applications in the Cross-Reference to Related Applications, Applicants first introduced the terminology "zero-profile" relating to spinal fusion devices. Applicants also have described zero-profile non-expandable and expandable stand-alone intervertebral spinal fusion device embodiments with incorporated BDFT screws. As described in greater detail below, exemplary embodiments of advanced ZP-EIS devices with BDFT screws are provided which have an improved contoured body with tapered edges to more precisely insert into and conform to the biconcave disc space. The present application also provides exemplary embodiments of more advanced ZP-EIS devices without accompanying BDFT screws each with very unique calibrated expandable mechanisms allowing minimally invasive intervertebral expansion, vertebral body distraction and segmental spinal fusion. An exemplary embodiment of a universal tool also is described that can be adapted to implant one or more (e.g., all) of the intervertebral device embodiments herein described into the intervertebral space, and mechanically expand them.

BACKGROUND

The history and evolution of instrumented spinal fusion in the entire human spine has been reviewed in Applicants' copending applications set forth in the Cross-Reference to Related Applications (for example in U.S. Ser. No. 11/536, 815, filed on Sep. 29, 2006, and Ser. No. 11/208,644, filed on Aug. 23, 2005). Currently, the majority of spinal fusion techniques are typically supplemented with posterior pedicle screw placement and/or anterior (or lateral) plating. Complications of pedicle screw placement in the spine may include duration of procedure, significant tissue dissection and muscle retraction, misplaced screws with neural and/or vascular injury, excessive blood loss, need for transfusions, prolonged recovery, incomplete return to work, and excess rigidity leading to adjacent segmental disease requiring further fusions and re-operations. Recent advances in pedicle screw fixation including minimally invasive and image-guided technology, and the development of flexible rods, imperfectly may address some but not all of these issues.

Anterior/and or lateral plating because of the plates' elevated profiles can be complicated by esophageal, or major vascular injury. The zero-profile devices described herein with reference to the exemplary embodiments avoid these complications.

Current non-expandable intervertebral spacers must be manufactured with different heights, and the most appropriate sized spacer is selected for insertion. In these situations, the vertebral bodies are forcefully distracted to allow placement of an imperfectly fitting spacer. These are most often supplemented with pedicle screw and/or or plate fixation.

SUMMARY

The exemplary embodiments described herein can allow a more precisely tailored complimentary fit between spacer and disc space, allowing the spacer to expand gradually in a calibrated manner, and to incrementally achieve the precise fit and degree of distraction desirable. Thus, the process according to the present invention can be more individualized for every patient and apply less forceful disruption to the intervertebral space thereby improving safety and enhancing effectiveness of the placement of intervertebral spacers. The exemplary embodiments are zero-profile, and thus, do not damage or indent overlying soft tissue or vascular structures further decreasing morbidity.

Herein described are exemplary embodiments of multiple ZP-EIS devices which combine in a single construct the dual functions of calibrated expandable intervertebral spacer distraction maintaining disc space height, and simultaneous segmental vertebral body spinal fusion.

To achieve safe, effective zero-profile and minimally invasive segmental spinal fusion, the exemplary embodiments of the present invention use of novel zero-profile calibrated expandable spacer (ZP-EIS) devices with or without BDFT screws which can be strategically inserted into the intervertebral disc space via anterior, anterio-lateral, lateral, far lateral or posterior surgical approaches.

In Applicants' applications set forth in the Cross-Reference to Related Applications, exemplary embodiments are directed to expanding intervertebral spacers which incorporated BDFT screws. One of these embodiments includes two sliding triangular bases to house two screws driven in two opposing directions which can be expanded in two simultaneous directions, height and depth, by turning a built-in screw adjuster. This was facilitated by a combined external drill/screw guide/cage expander to further enhance trajectory precision and to simultaneously expand the screw box in height and depth to custom-fit the individual disc space height. Applicants' copending applications set forth in the Cross-Reference to Related Applications further describe an exemplary embodiment of a universal tool and the adaptability of the tool, for example, to exemplary embodiments of sliding boxes, as well as to the exemplary embodiments described herein, including those with and without BDFT screws.

The evolved zero-profile expandable intervertebral spacer (ZP-EIS) embodiments with incorporated BDFT screws presented herein are more finely tapered and contoured to more easily allow insertion and conformation to the biconcave disc space.

The exemplary embodiments of ZP-EIS devices without incorporated BDFT screws described herein have the ability to incrementally and uniformly separate and distract the vertebral bodies. Each embodiment has a very unique mechanically designed mechanism of incremental expansion. The devices are all designed with cavities for bone fusion giving the surgeon the option to use these as stand-alone fusion/spacer devices or as supplemental devices if other screw fixation is deemed necessary. These innovations represent a continued evolution of our concept of zero-profile calibrated expandable intervertebral distraction/fusion spacers described in Applicants' applications, for example, as set forth in the Cross-Reference to Related Applications.

In the exemplary ZP-EIS embodiments with incorporated BDFT screws, a rostral-directed screw is passed through one built-in screw guide of the device which then is inserted and screwed into the superior vertebral body. Next, a caudally directed screw is passed through an adjacent built-in screw guide, which then is inserted and screwed into the inferior vertebral body. One of many novels features of this design is the built-in prescribed angles of the integral screw guides which allow the transvertebral penetration into the vertebral bodies. This is a truly amazing feat accomplished particularly in the posterior or lateral/far lateral lumbar spine considering the small anatomically restricted work zone within which to work, which is very narrowly prescribed by obtuse angulations between screw and intervertebral bone surfaces, and by nerve root, facet joint and pedicle. Applicants' applications set forth in the Cross-Reference to Related Applications included an angled screw driver specifically designed to fit these devices if a straight screw driver impedes screw placement. Hence, these external tools can provide the means in any circumstance to accomplish precision screw trajectory.

The exemplary zero-profile embodiments of the present invention can provide enhanced individualized intervertebral conformation, and multiple methods of finely calibrating intervertebral expansion, and vertebral body distraction further reducing morbidity and enabling more minimally invasive surgical methods of vertebral body distraction and segmental fusion compared to Applicants' applications set forth in the Cross-Reference to Related Applications.

The exemplary embodiments of box casings can include perforations to allow bone packing for fusion. These exemplary devices can prevent subsidence. In an exemplary embodiment, both the inside of the denuded intervertebral space, and the devices can be packed with autologous or allograft bone, BMP, DBX or similar osteoconductive material.

The zero-profile EIS embodiments, in particular those with incorporated BDFT screws, can provide as strong or stronger segmental fusion as pedicle screws without the complications arising from pedicle screw placement which include screw misplacement with potential nerve and/or vascular injury, violation of healthy facets, possible pedicle destruction, blood loss, and overly rigid fusions. In the case of the posterior Lumbar spine by placing screws across the intervertebral space from vertebral body to vertebral body, engaging anterior and middle spinal columns, and not the vertebral bodies via the transpediclar route, the healthy facet joints, if they exist, are preserved. Because the exemplary techniques accomplish both anterior and middle column fusion, without rigidly fixating the posterior column, the exemplary embodiments in essence create a flexible fusion. This exemplary devices therefore can provide a flexible fusion device because the preserved posterior facet joints retain their function achieving at least a modicum of mobility and hence a less rigid (i.e. a flexible) fusion.

The very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in operating room (O.R.) time. Thus, the complication of pedicular screw pull-out and hence high re-operation rate associated with the conventional flexible fusion pedicle screws/rods is obviated.

Although the exemplary embodiments can be supplemented with transpedicular screws, there would be no absolute need for supplemental pedicle screw fixation with these operative techniques. The expandable spacers without BDFT screws can be supplemented with other screw stabilization if desired.

Because the exemplary embodiments are zero-profile, these devices also obviate the morbidity involved with profiled anterior or lateral plating. Multi-level fusions can be performed with all of the exemplary embodiments described herein.

Currently failed anterior lumbar arthroplasties are salvaged by combined anterior and posterior fusions. The exemplary ZP-EIS embodiments with incorporated BDFT screws could be utilized as a one-step salvage operation for failed/extruded anteriorly placed lumbar artificial discs obviating the above salvage procedure which has far greater morbidity.

BRIEF DESCRIPTION OF DRAWINGS

These and other aspects and features of embodiments of the present invention will be better understood after a reading of the following detailed description, together with the attached drawings, wherein:

FIGS. 8D(i) and 8D(ii) illustrate superior oblique perspective views of the positioning tool/drill guide/box expander component, according to an exemplary embodiment, which may be optionally used for the exemplary embodiments illustrated in FIGS. 1A-1B and 2A-2D.

DETAILED DESCRIPTION OF THE INVENTION

Figure 1A:
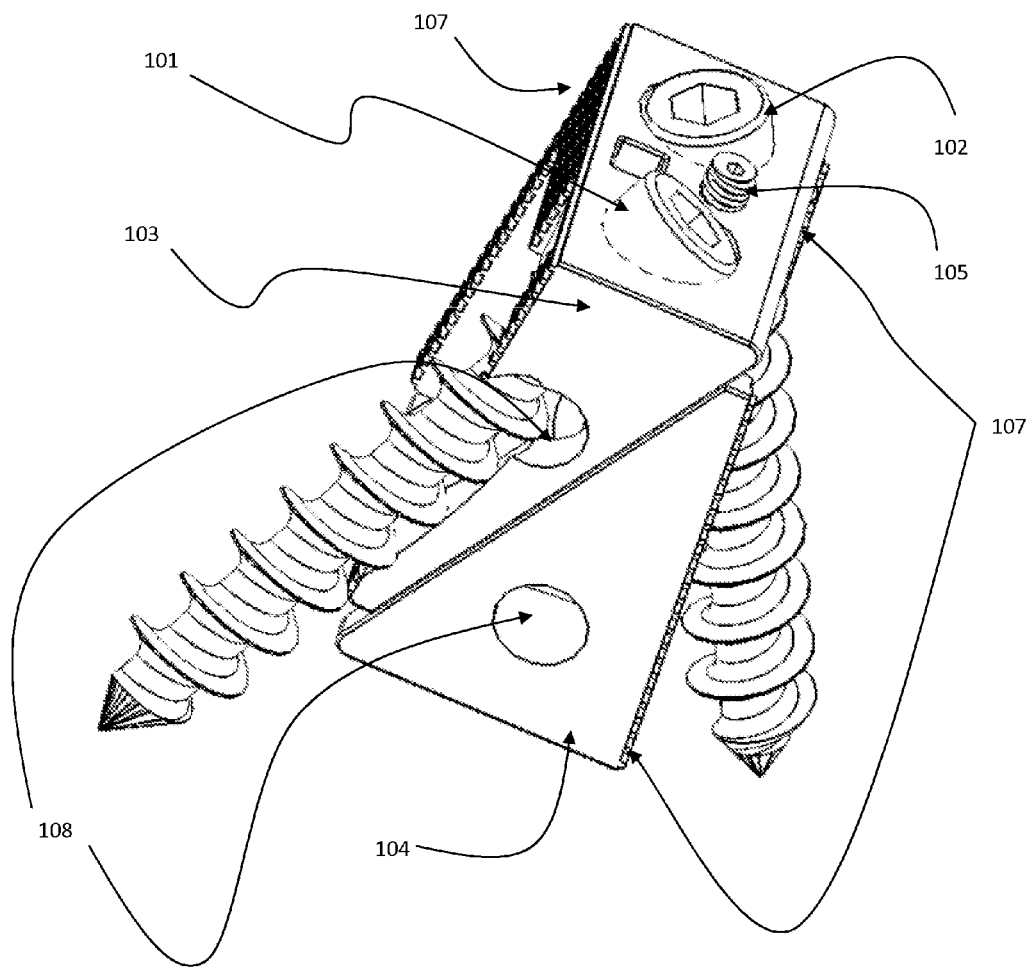
FIGS. 1A-1B illustrate an exemplary embodiment (Embodiment I) of a non-tapered sliding base ZP-EIS device with incorporated BDFT screws in sagittal-oblique (FIG. 1A), and exploded (FIG. 1B) views.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

1. The Medical Device

Referring now to the drawings, FIGS. 1A-8K illustrate exemplary embodiments of ZP-EIS devices that can solve the above described problems and others in the spine by insertion of the ZP-EIS devices into the denuded intervertebral disc space according to the features illustrated in the exemplary embodiments (I-VII).

Figure 1B:
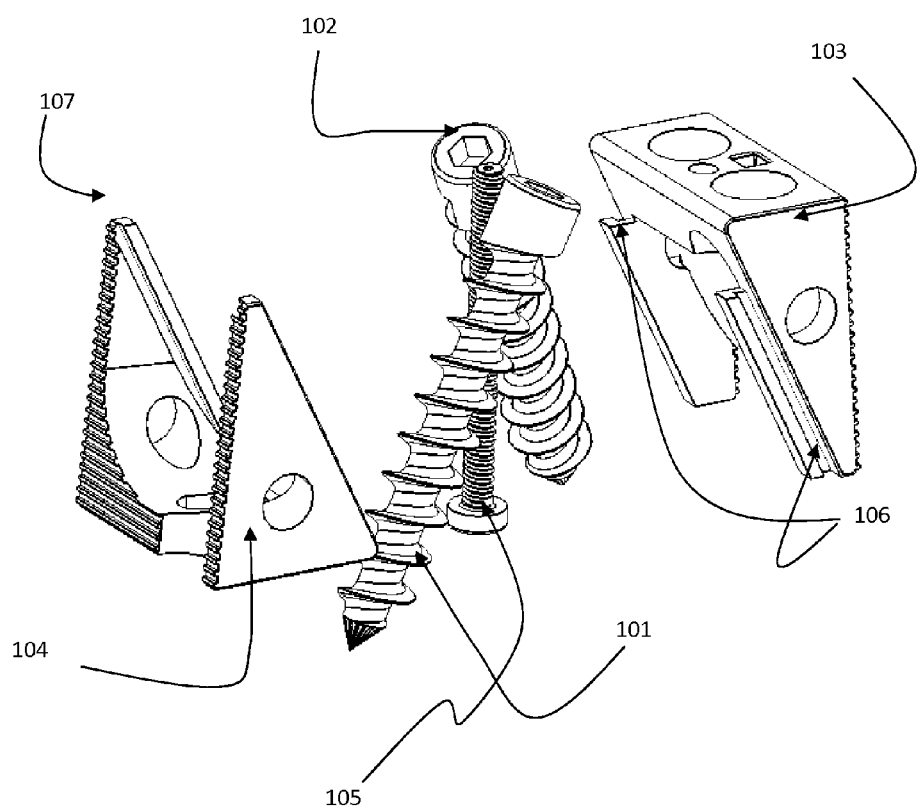
Figure 2A:
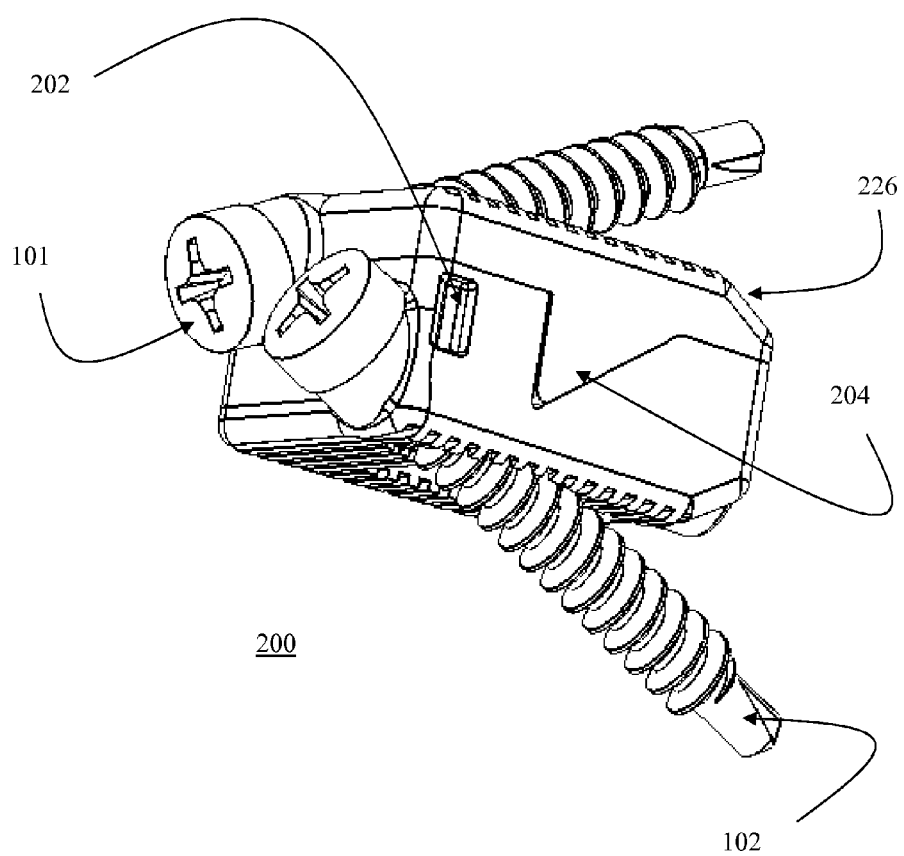
FIGS. 2A-2D illustrate an exemplary embodiment (Embodiment II) of a tapered sliding base ZP-EIS device with incorporated BDFT screws in closed (FIG. 2A), semi-expanded (FIG. 2B), and fully expanded (FIG. 2C) positions, and in an exploded view (FIG. 2D).
Figure 2B:
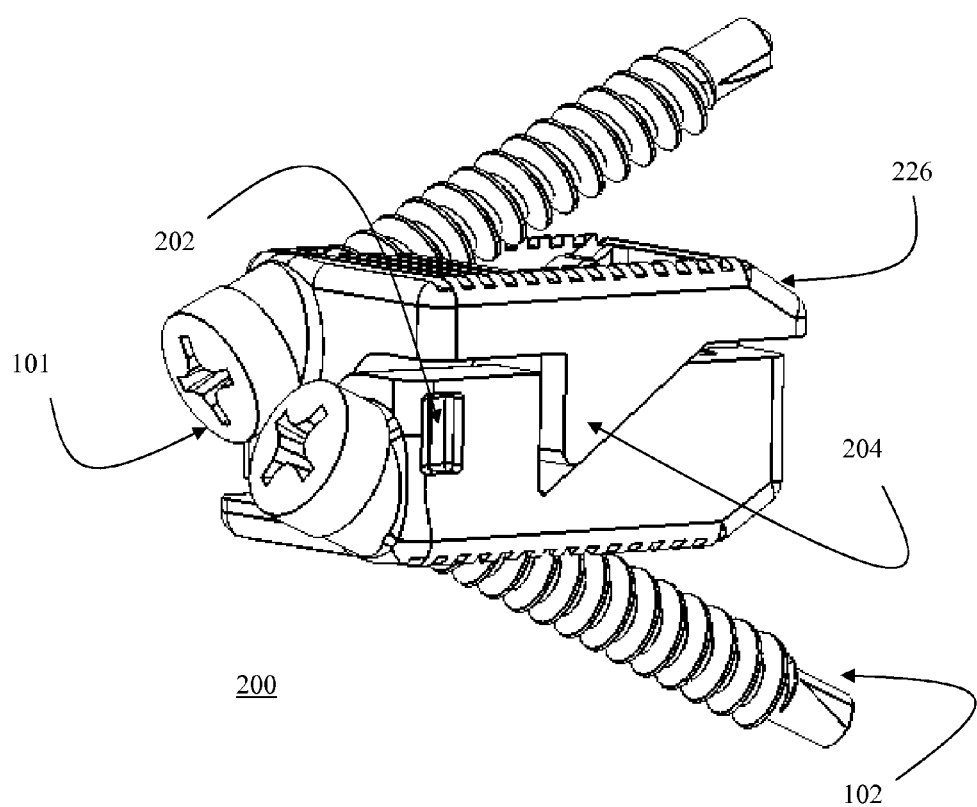
Figure 2C:
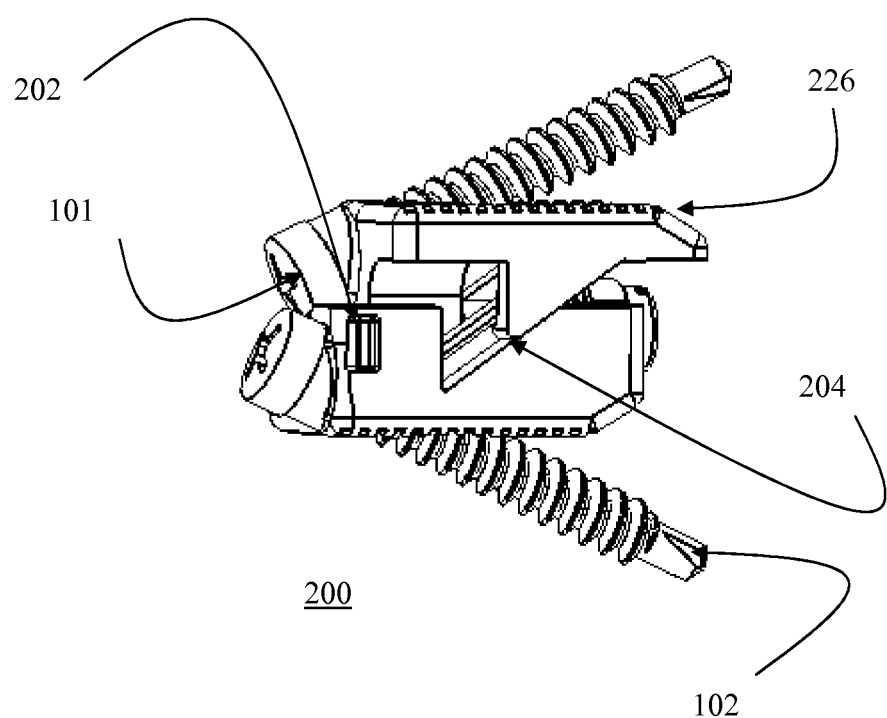
Figure 2D:
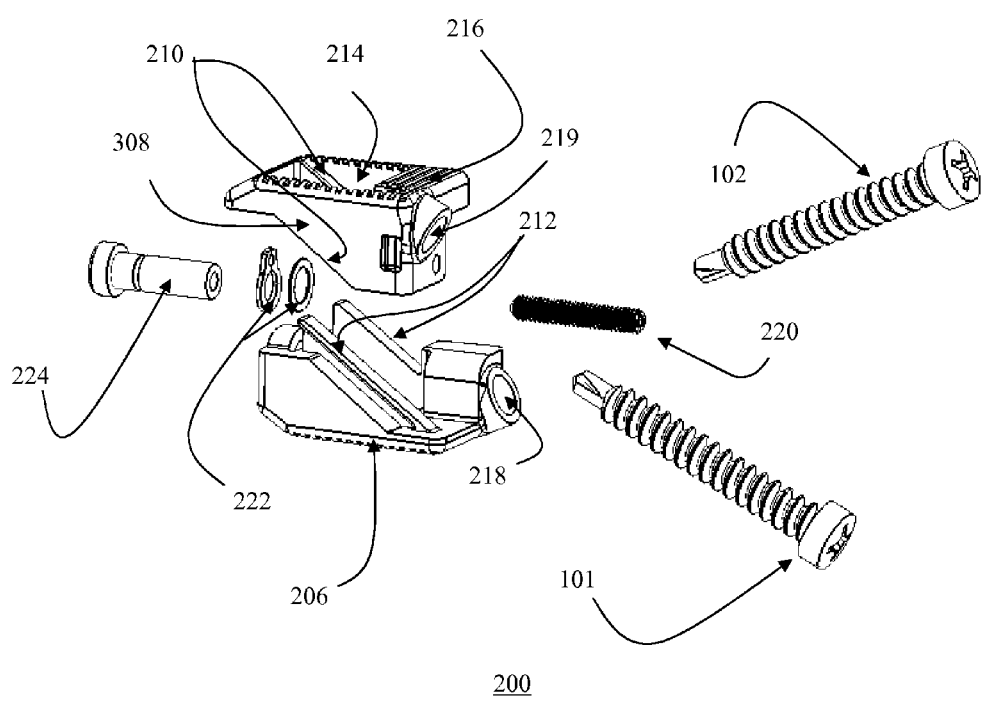
Figure 3A:
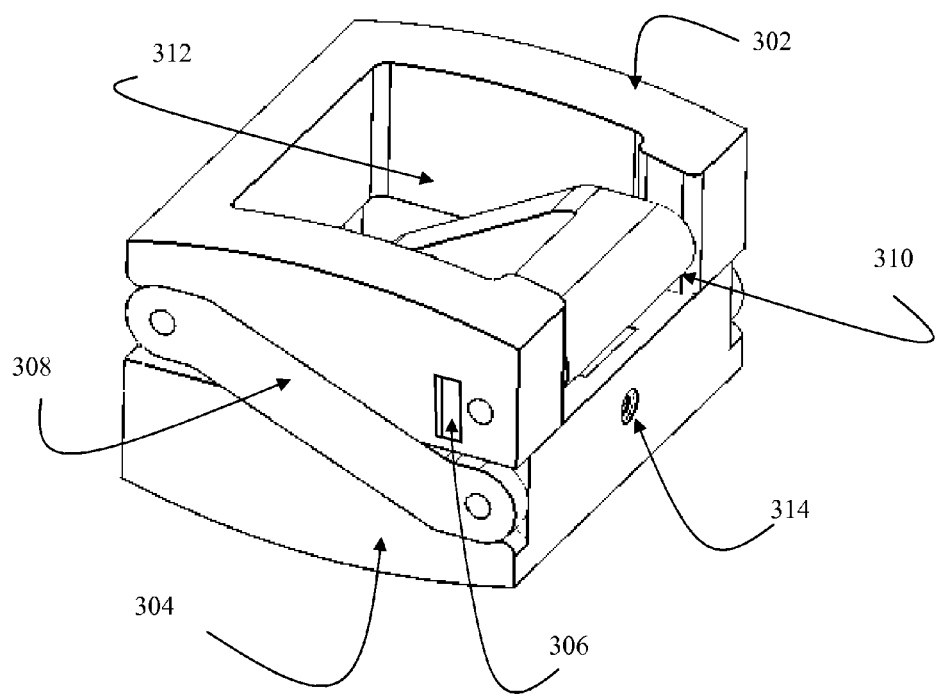
FIGS. 3A-3D illustrate an exemplary embodiment (Embodiment III) of a scissors jack driven ZP-EIS device without incorporated BDFT screws in closed (FIG. 3A), semi-expanded (FIG. 3B), and fully expanded (FIG. 3C) positions, and in an exploded view (FIG. 3D).
Figure 3B:
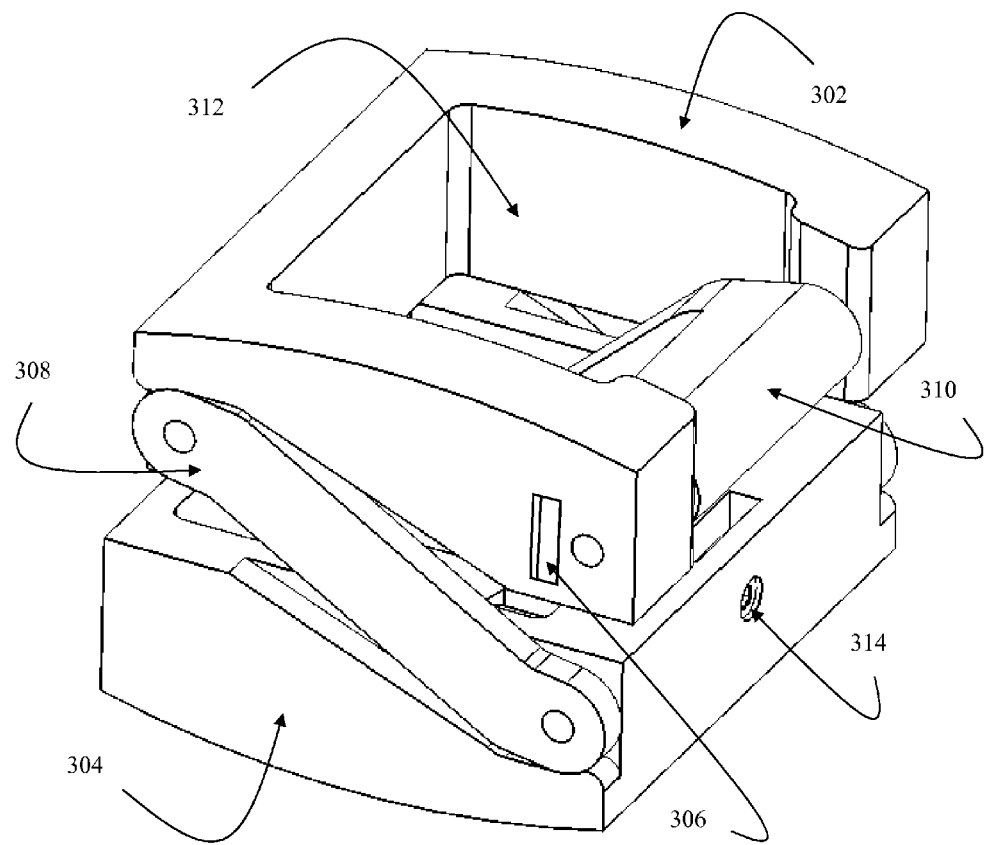
Figure 3C:
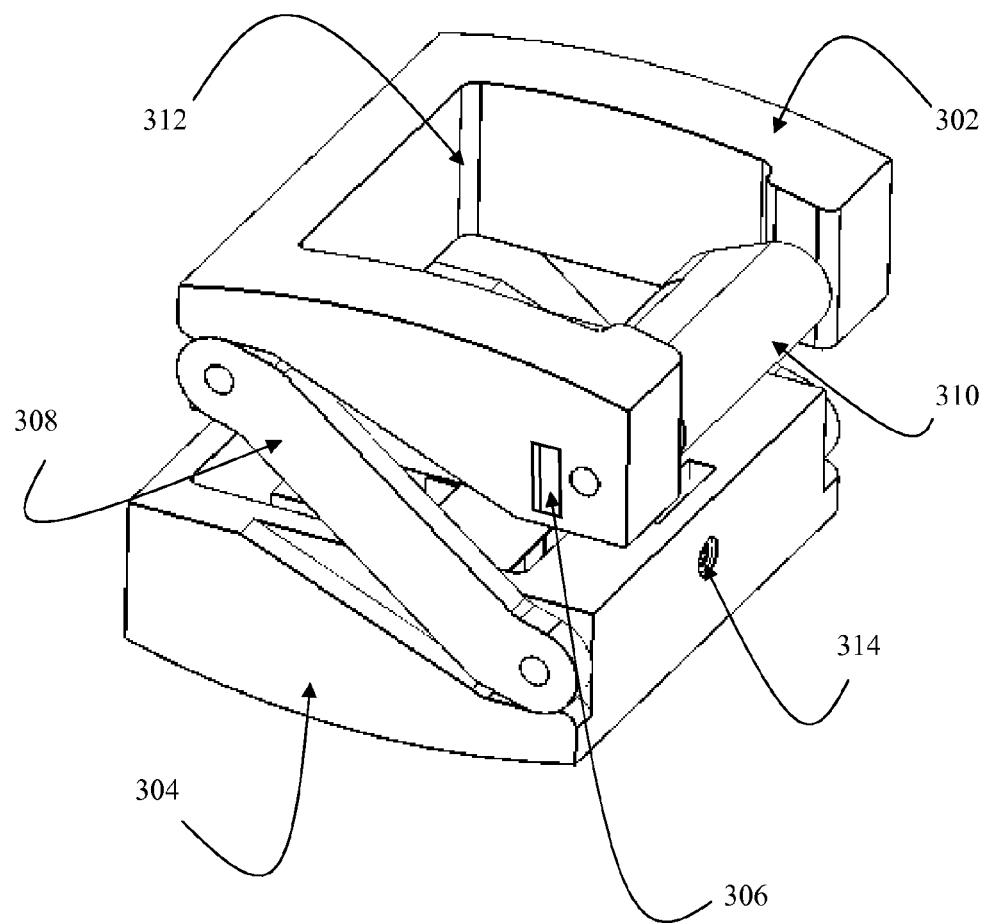
Figure 3D:
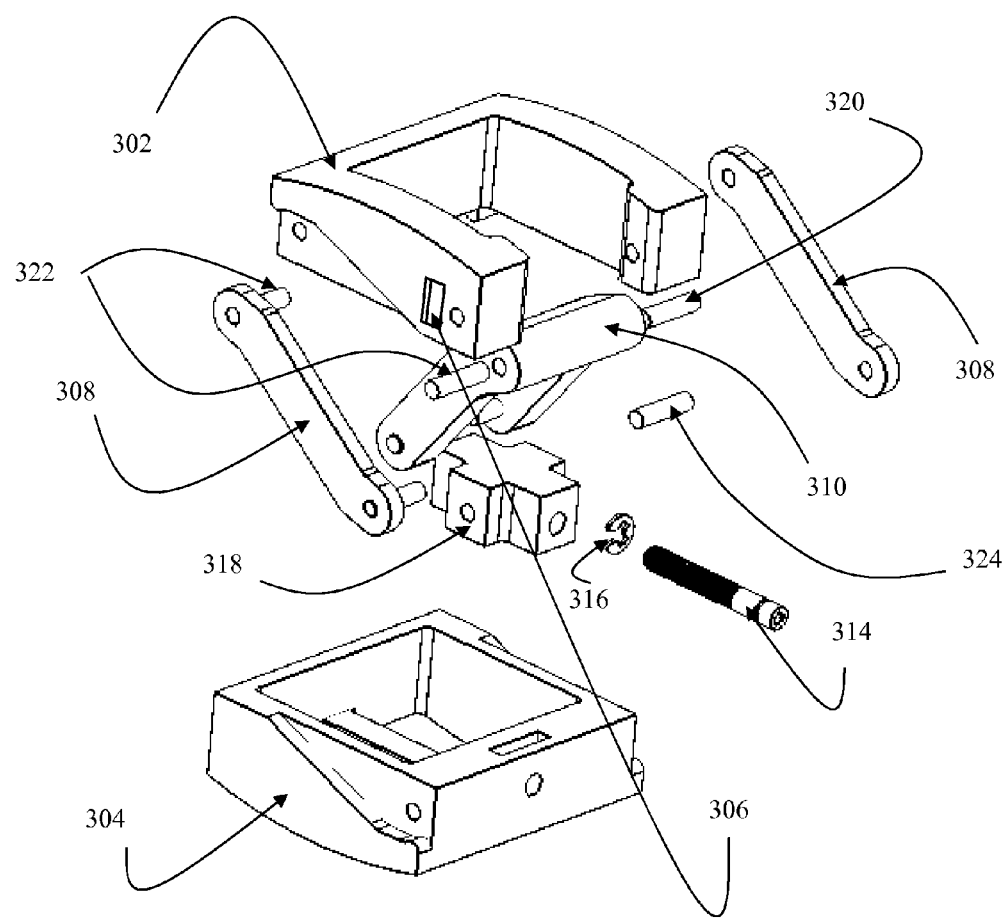

FIGS. 1A-1B illustrate three-dimensional views of a ZP-EIS device 100 according to embodiment I, with two BDFT screws 101, 102.

The expandable ZP-EIS device 100 includes of top and bottom triangular sliding bases 103, 104 (FIGS. 1A-1B). The superior and inferior segments of the height/depth adjusting screw 105 are integrated and connected to the two separate top and bottom triangular bases 103, 104, respectively. By turning this adjusting (rotation) screw 105 back and forth, i.e. clock-wise, and counter clockwise, the sliding rails 106 of the top triangular base 103 (FIGS. 1A-1B) slide up and down the rail inserts 107 on the bottom triangular base 104 (FIGS. 1A-1B). This action will simultaneously alter the intervertebral height and depth of the device 100 allowing individualized custom fitting of the ZPEIS device 100 conforming to the dimensions of the disc space.

A transvertebral screw 101 penetrates the top base 103, and a transvertebral screw 102 traverses the bottom base 104 of the screw box (device 100). The two screws 101, 102 traverse the screw box 100 in opposing directions, bi-directionally. The external edges of the triangular bases 103, 104 in contact with vertebral body surfaces can include ridges 107, which facilitates the ZP-EIS device 100 incorporation into and fusion with the superior and inferior vertebral bodies (FIGS. 1A-1B). Both top and bottom ZP-EIS bases 103, 104 can be perforated with holes 108 to allow bone placement for fusion. In an exemplary embodiment, the entire construct, furthermore, can be hollow to allow filling with bone filling material. Hence, the exemplary device functions as both an intervertebral bone fusion spacer and bi-directional transvertebral screw fusion device.

FIGS. 2A-2D illustrate a ZP-EIS device 200 according to exemplary embodiment II. This exemplary device 200 incorporates BDFT screws and employs a fusion wedge mechanism of expansion.

The device 200 includes a contoured top 208 and bottom 206 housing which have tapered edges and are coupled to each other by a diagonal dovetail interface 204 which constrains the components 208, 206 to translate linearly relative to each other. The linear translation causes a vertical separation of the top 208 and bottom 206 housing surfaces which are parallel to each other. The position is secured and adjusted by a threaded rotation screw 220 coupled to a nut 224 and a retaining ring 222 and passed through the top 208 and bottom 206 housing pieces. As the threaded rotation screw 220 is rotated further into the nut 224, the housing pieces 208, 206 expand vertically.

By turning this adjusting (rotation) screw 220 back and forth i.e. clock-wise, and counter clockwise, the sliding rails 210 of the top housing piece 208 slide up and down the rail inserts 212 on the bottom housing piece 206. This action will simultaneously alter the intervertebral height and depth of the device 200 allowing individualized custom fitting of the ZP-EIS conforming to the dimensions of the disc space. A transvertebral screw 101 penetrates the top housing piece 208, and a transvertebral screw 102 traverses the bottom housing piece 206 of the device 200. The two screws 101, 102 traverse the device 200 in opposing directions, bi-directionally. The external edges of the housing pieces in contact with vertebral body surfaces include ridges 216. This facilitates the ZP-EIS device 200 incorporation into and fusion with the superior and inferior vertebral bodies (FIGS. 2A-2D). Both top and bottom ZP-EIS housing bases 208, 206 are perforated with holes 214 to allow bone placement for fusion. The entire device 200, furthermore, can be hollow to allow bone filling. Hence, the exemplary device 200 functions as both an intervertebral bone fusion spacer and bi-directional transvertebral screw fusion device.

The device 200 can include a tapered edge 226 (shown for example in FIGS. 2A-2B), which allows easier introduction and insertion of the device 200 into the disc space.

FIGS. 3A-3D illustrate a ZP-EIS device 300 according to exemplary embodiment III, which employs a scissor jack expansion mechanism.

In this embodiment the top 302 and bottom 304 housing are attached by one internal linkage arm 310, and two external linkage arms 308. The device 300 can include indentations 306 on each lateral side close to the top of the device 300 to mate with the prongs of the universal tool (for example, as described in FIGS. 8A-8I) to assist in grasping, inserting and impacting the device 300. A lead screw or rotation screw 314 is mounted in the bottom housing 304 and secured in place with a retaining ring 316. When the lead (rotation) screw 314 is rotated by an external tool (for example, as described in FIGS. 8A-8I), the screw 314 causes the linear displacement of the separation block 318 which is hinged to the internal linkage 310. The horizontal motion of the separation block causes the top 302 and bottom 304 housing pieces to separate vertically. The separation distance depends on the amount of rotation of the lead (rotation) screw 314, and is limited by the freedom of the separation block 318 to move within the bottom housing 304. The exemplary embodiment can include a plurality of pins, such as eight pins 320, 322, 324, to secure the external linkage arms 308 to the top 302 and bottom 304 housing units and to the separation block 318. The top housing 302 and bottom housing 304 can include one or more cavities 312 for bone incorporation/fusion.

Figure 4A:
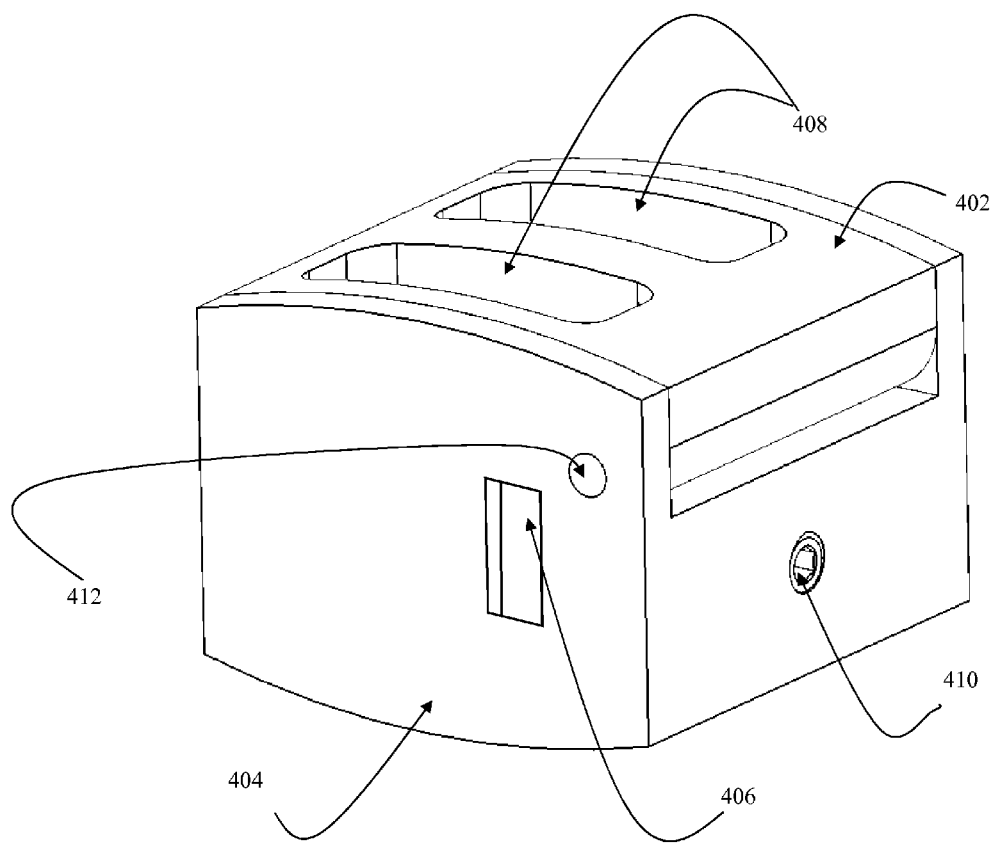
FIGS. 4A-4C illustrate an exemplary embodiment (Embodiment IV) of a tapered thread driven ZP-EIS device without incorporated BDFT screws in closed (FIG. 4A), semi-expanded/fully expanded positions (FIG. 4B), and in cross-sectional view (FIG. 4C).
Figure 4B:
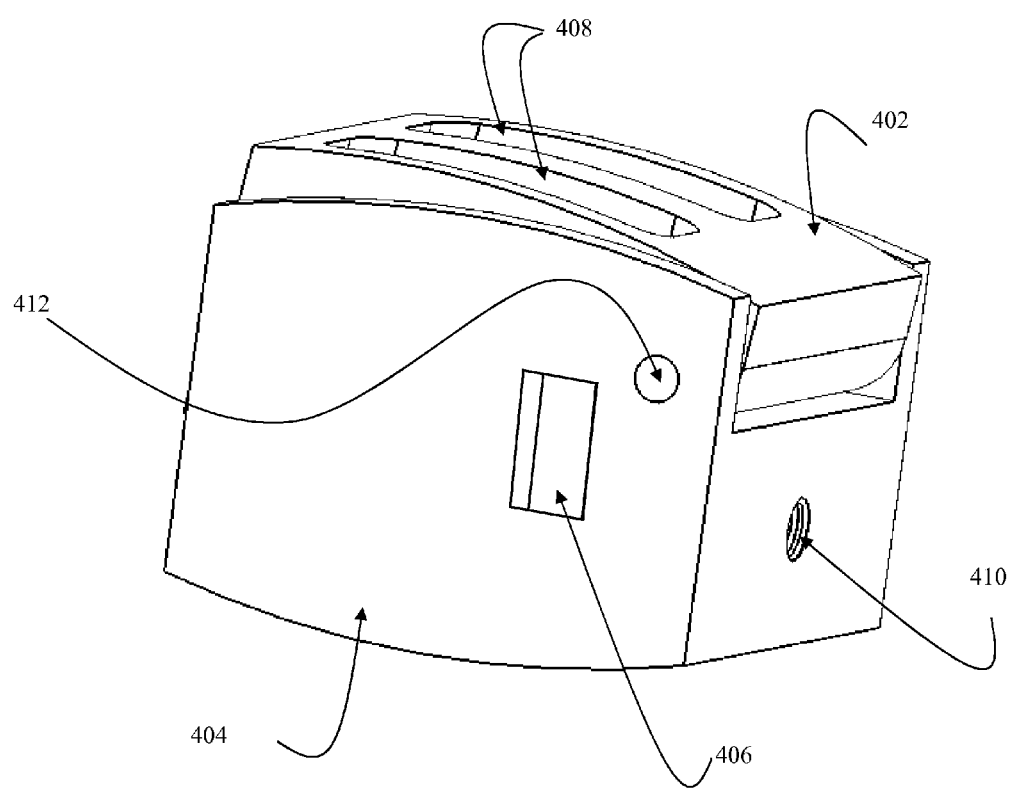
Figure 4C:
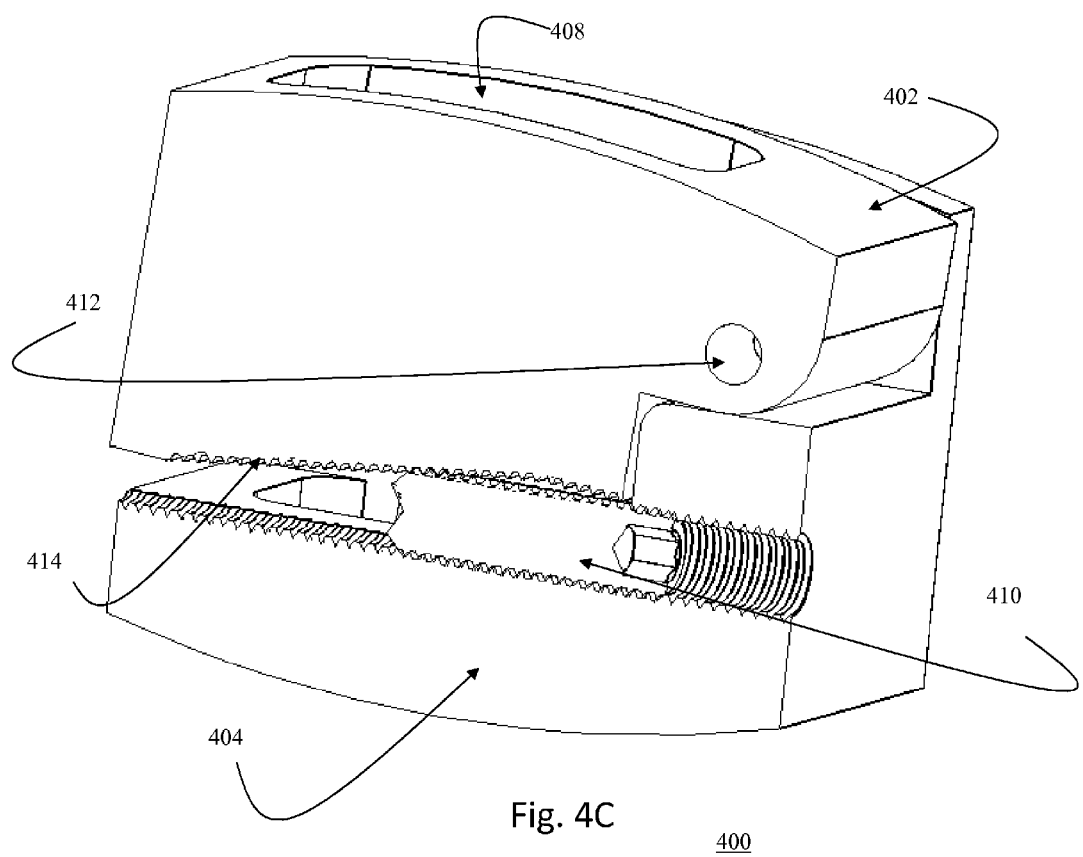
Figure 5A:
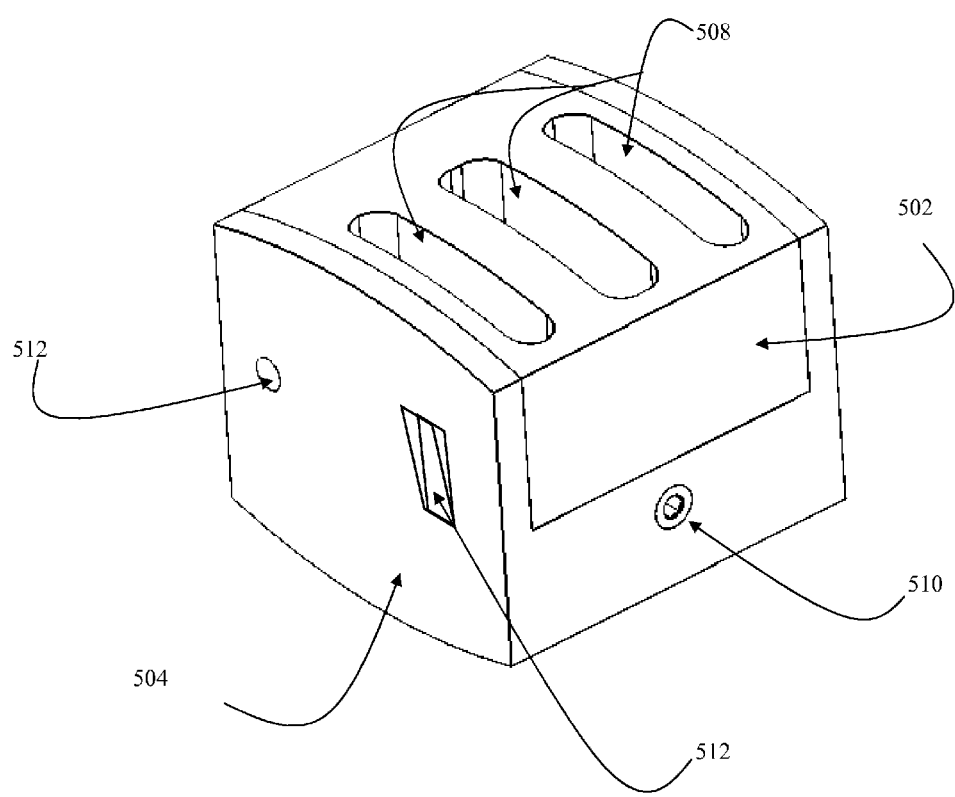
FIGS. 5A-5D illustrate an exemplary embodiment (Embodiment V) of a dry anchor driven ZP-EIS device without incorporated BDFT screws in closed (FIG. 5A), semi-expanded (FIG. 5B), and fully expanded (FIG. 5C) positions, and in an exploded view (FIG. 5D).
Figure 5B:
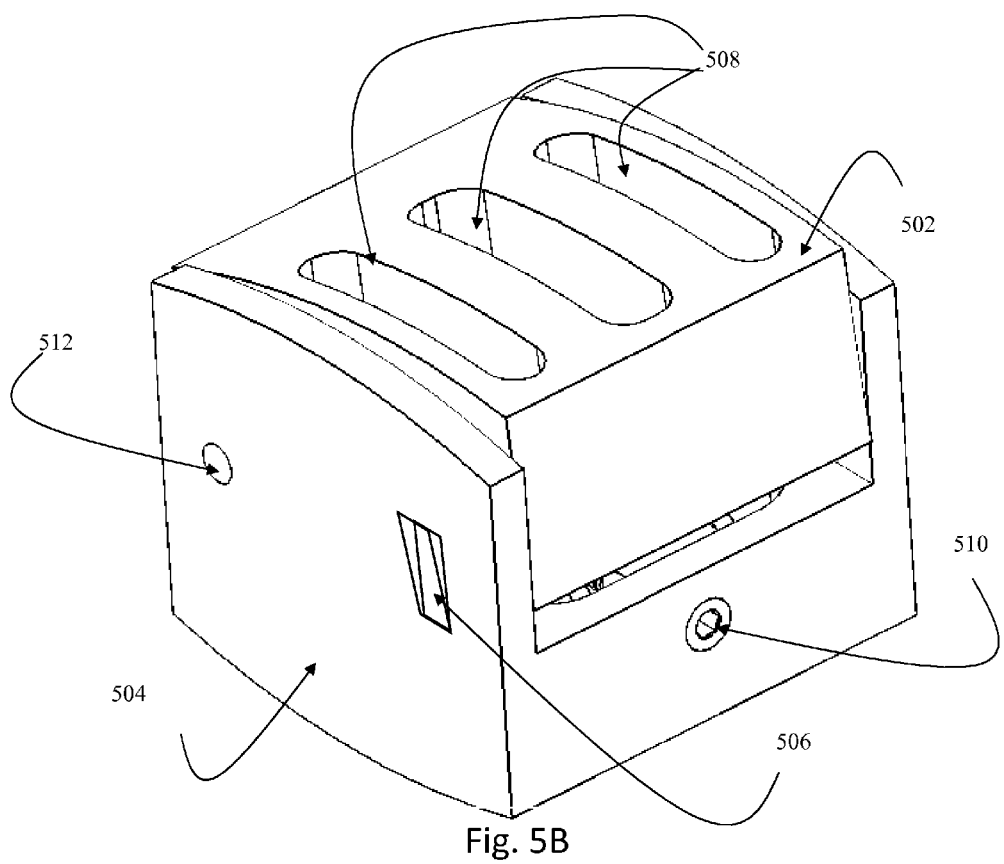
Figure 5C:
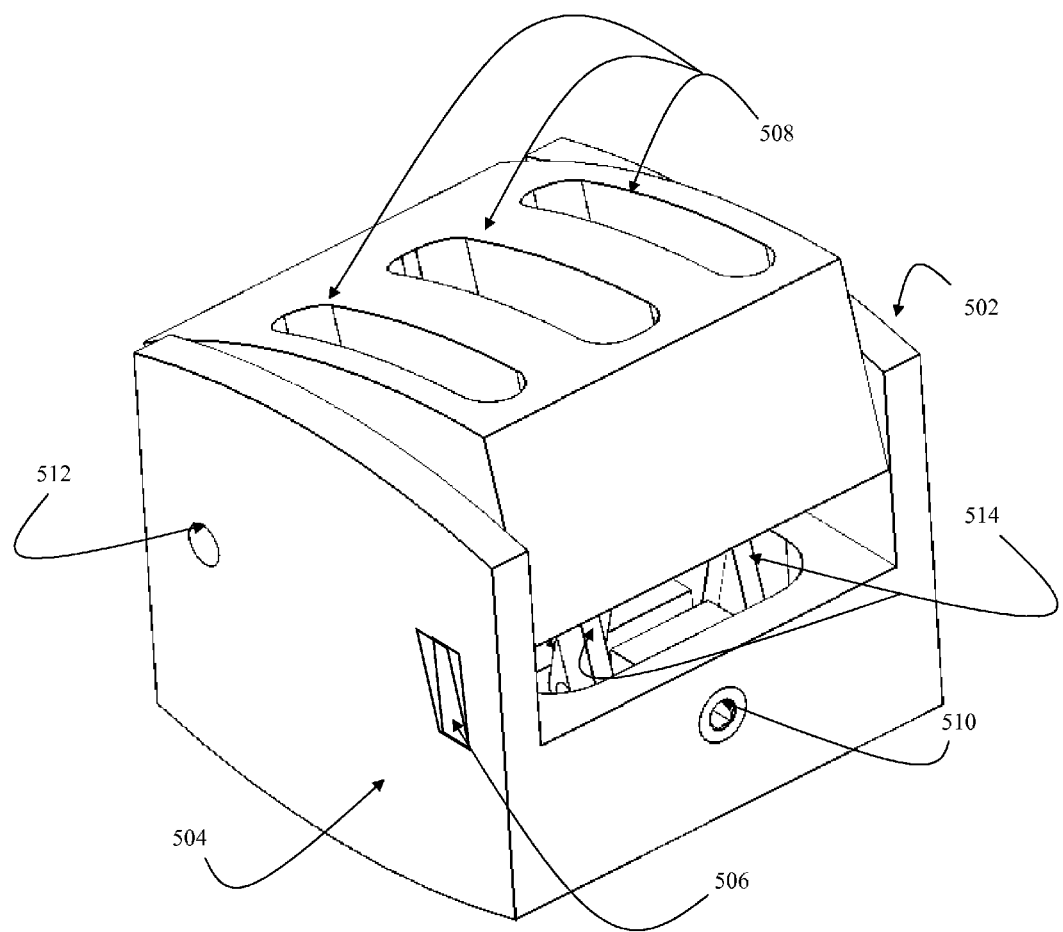
Figure 5D:
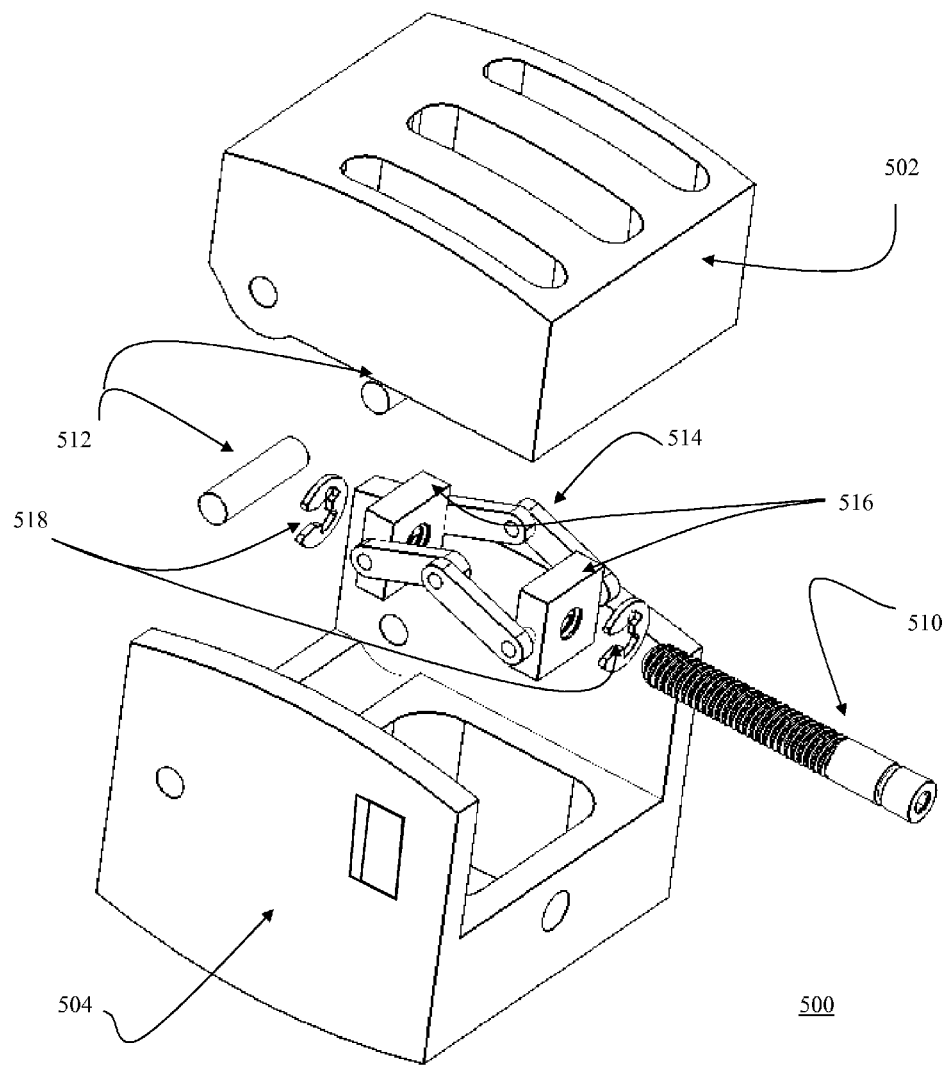
Figure 6A:
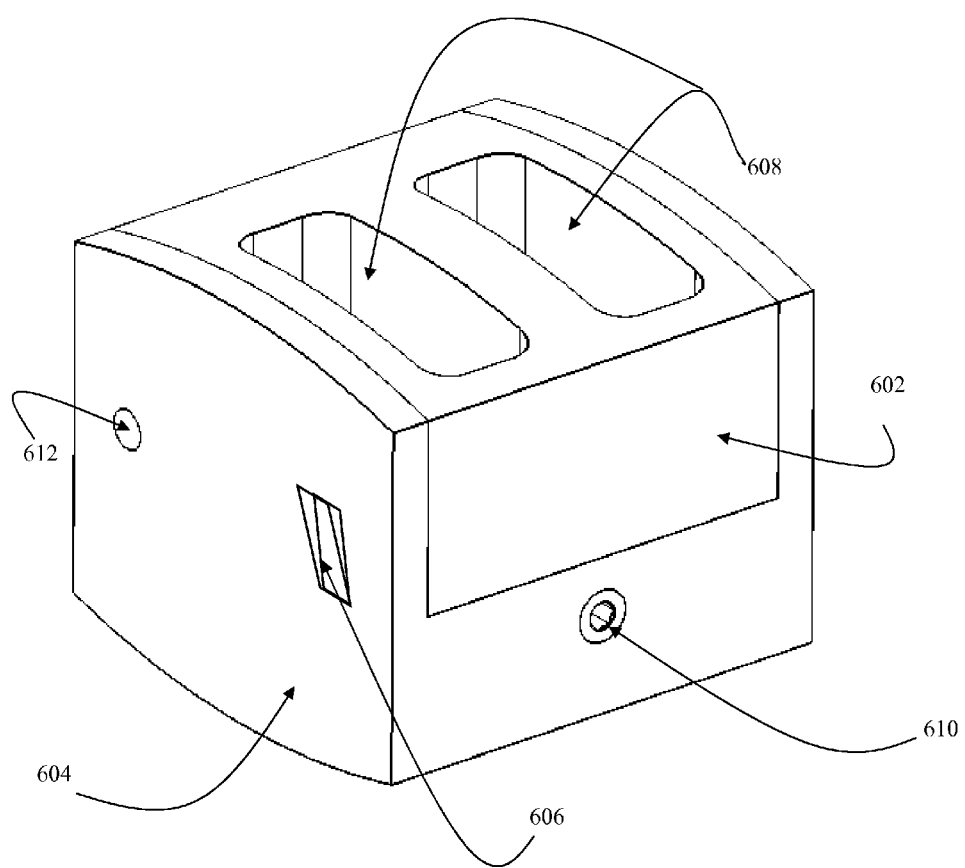
FIGS. 6A-6D illustrate an exemplary embodiment (Embodiment VI) of a modified wedge driven ZP-EIS device without incorporated BDFT screws in closed (FIG. 6A), semi-expanded (FIG. 6B), and fully expanded (FIG. 6C) positions, and in an exploded view (FIG. 6D).
Figure 6B:
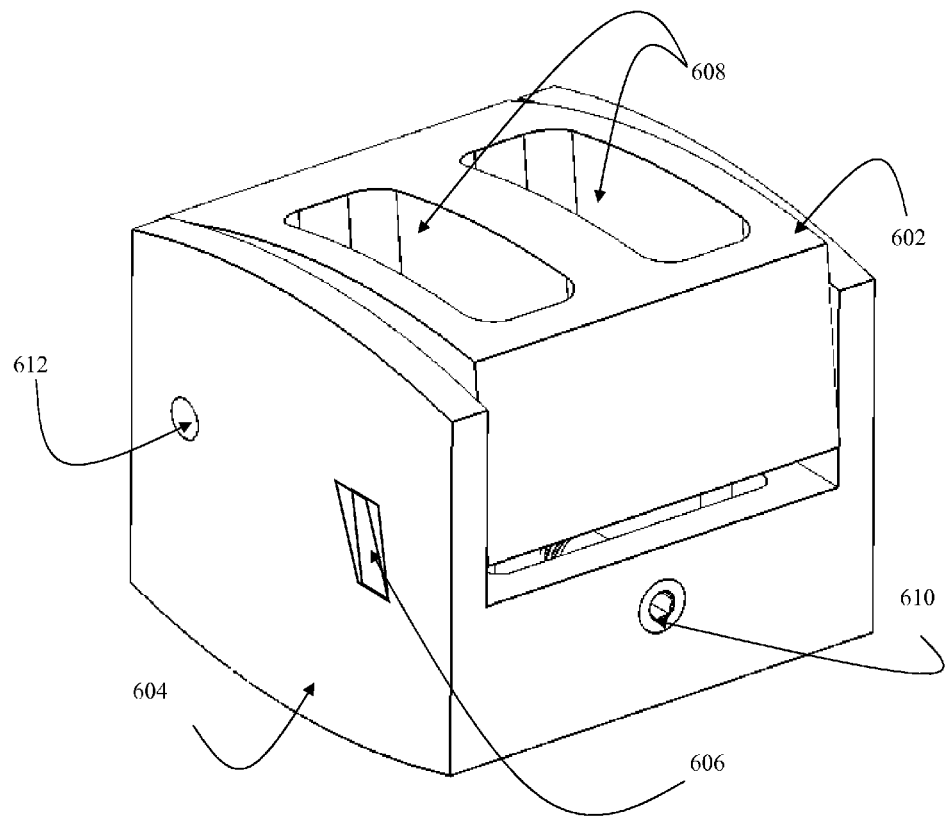
Figure 6C:
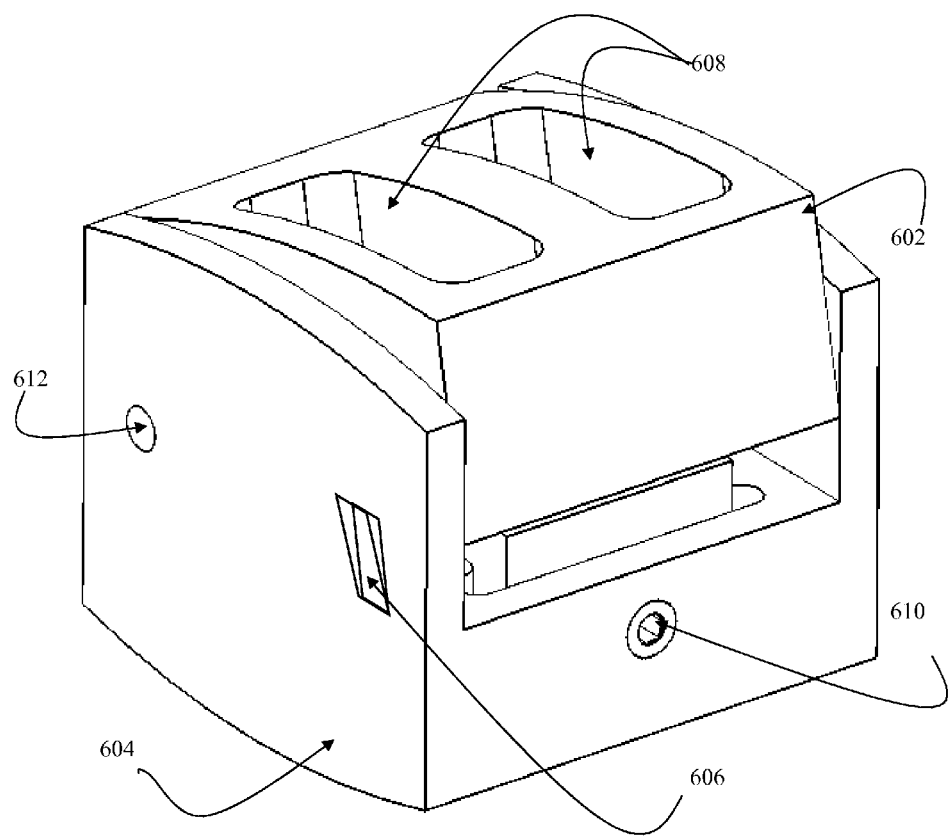
Figure 6D:
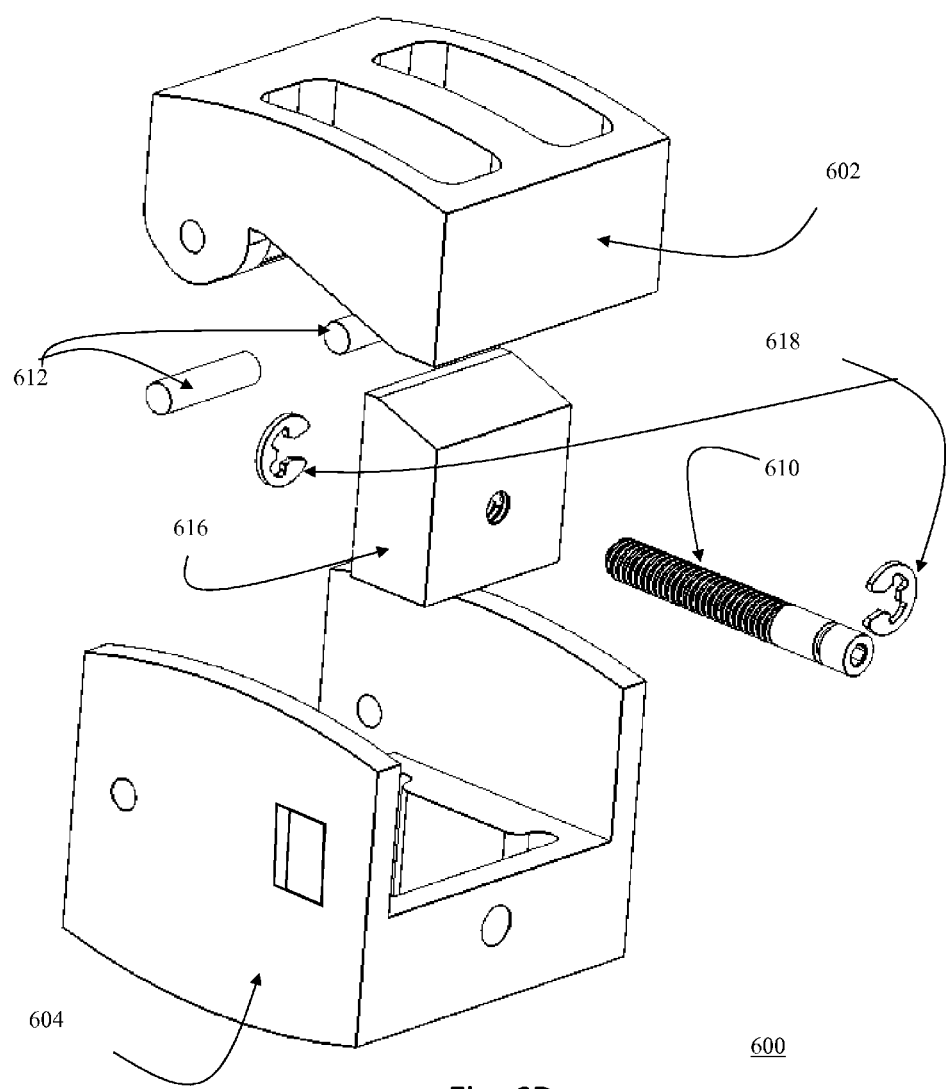
Figure 7A:
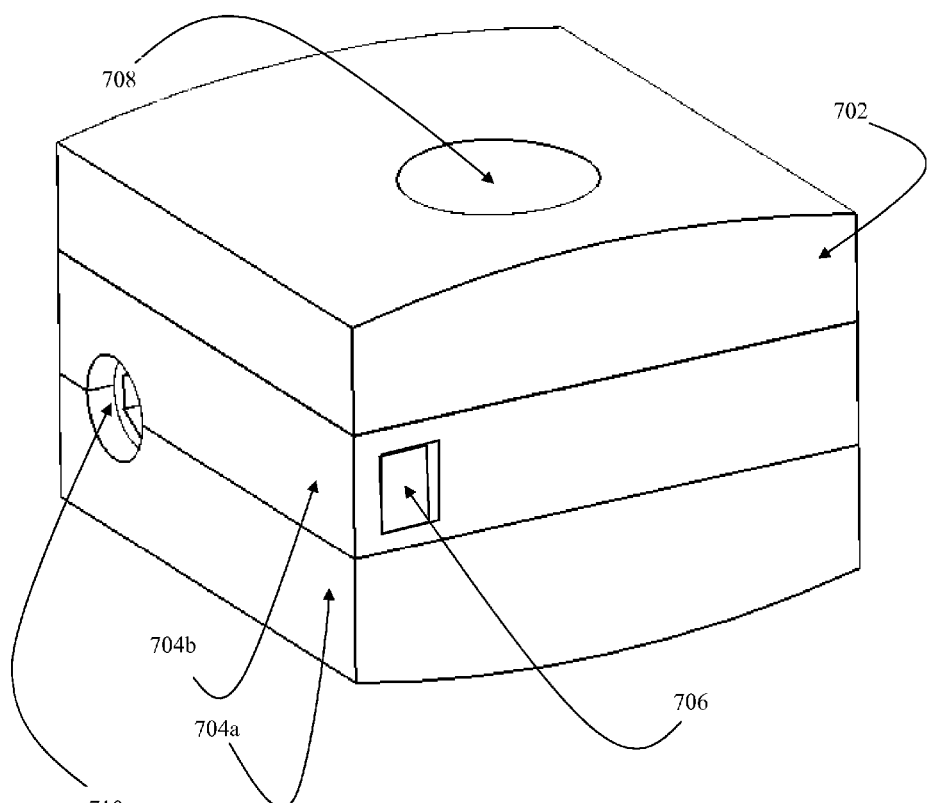
FIGS. 7A-7D illustrate an exemplary embodiment (Embodiment VII) of a worm drive ZP-EIS device without incorporated BDFT screws in closed (FIG. 7A), semi-expanded (FIG. 7B), and fully expanded (FIG. 7C) positions, and in an exploded view (FIG. 7D).
Figure 7B:
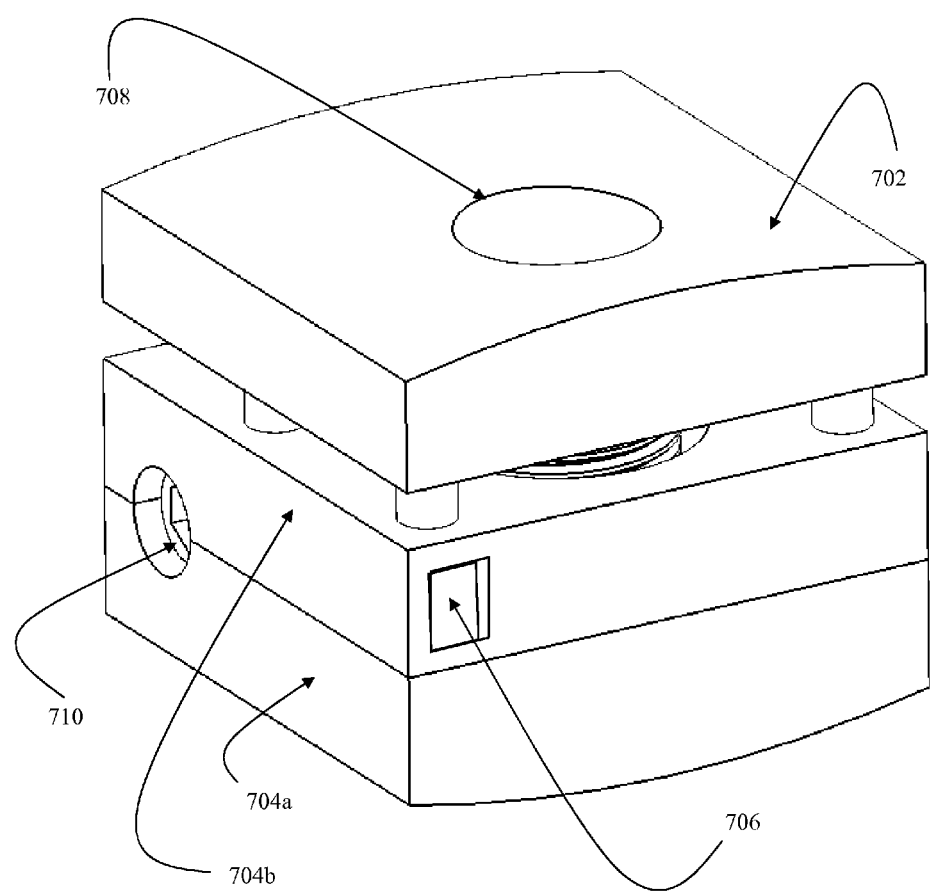
Figure 7C:
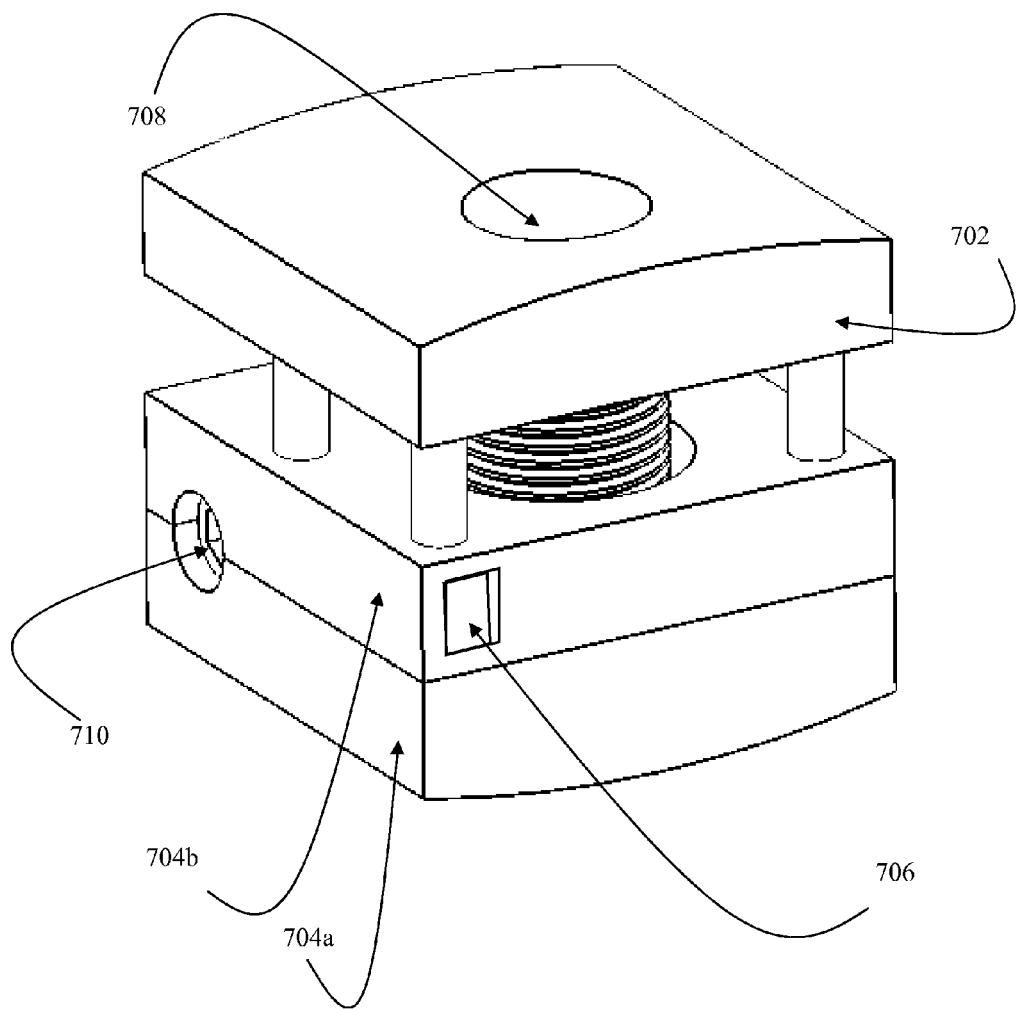
Figure 7D:
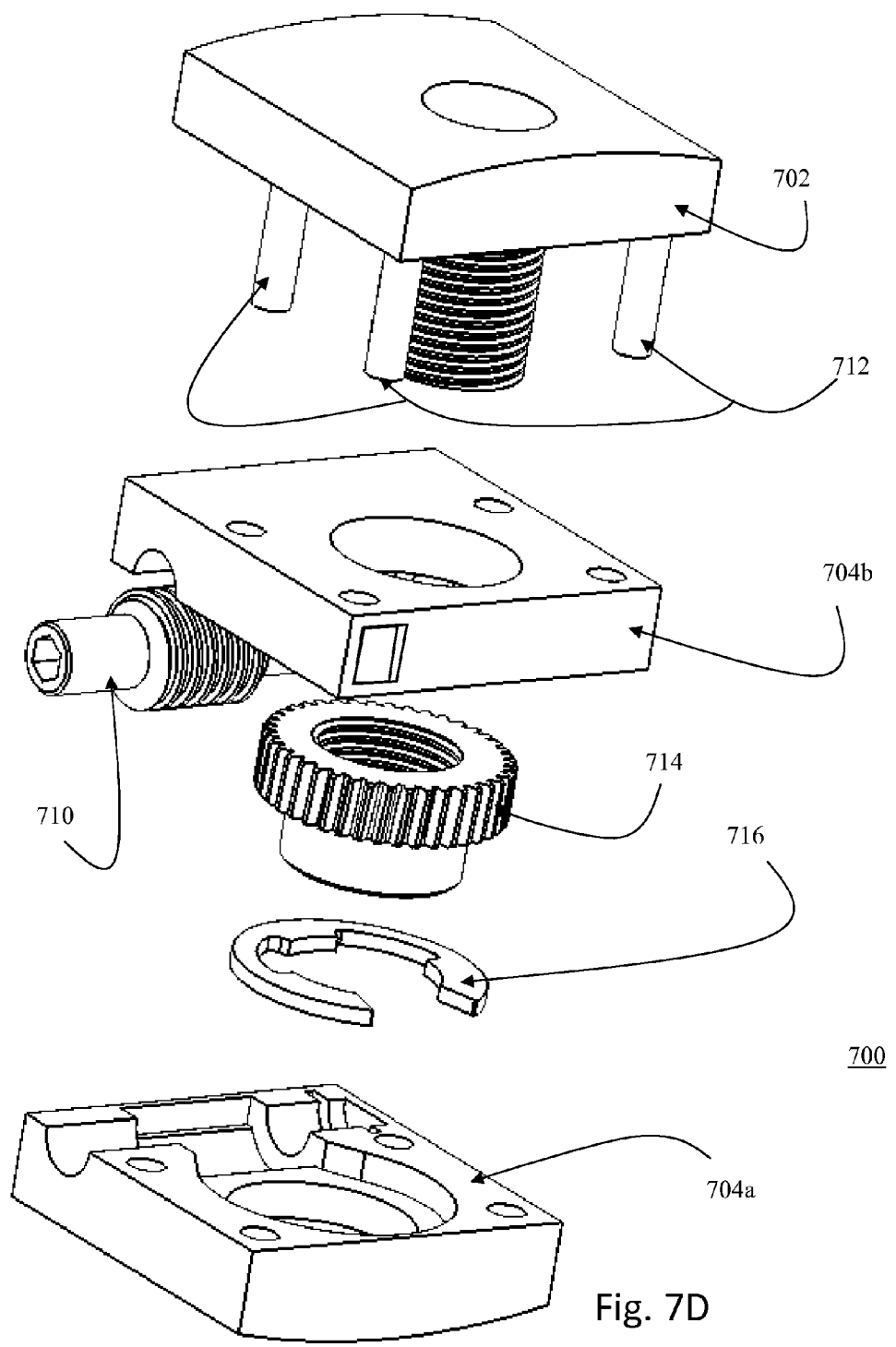
Figure 7E:
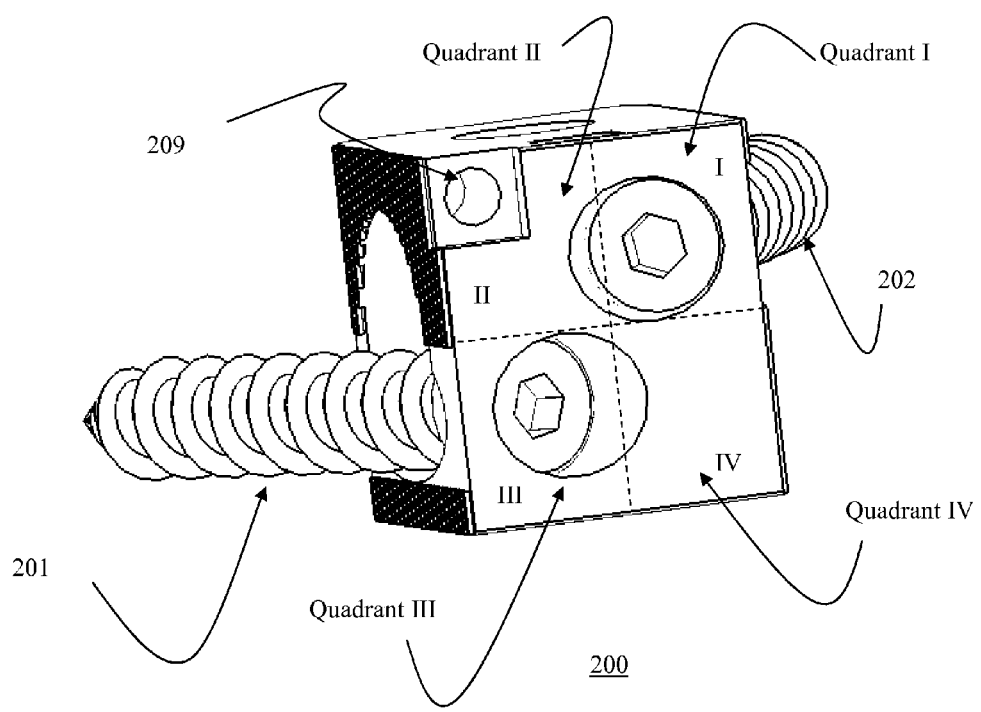
FIGS. 7E(i) and 7E(ii) illustrate top, perspective views of an intervertebral cage construct according to an exemplary embodiment of the invention.

FIGS. 4A-4C illustrate a ZP-EIS device 400 according to exemplary embodiment IV, which employs a tapered thread mechanism of expansion.

The exemplary device 400 can include a top housing 402 and bottom housing 404, which can be attached by one or more pins, such as two pins 412, which allow rotation of the top housing 402 and bottom housing 404 relative to each other about the axis of the pins 412. The top housing 402 and/o bottom housing 404 can include indentations 406 on their lateral sides close to the top of the device 400 to mate with the prongs of a tool or universal tool (e.g., prongs 806 in FIGS. 8A-8I) to assist in grasping, inserting and impacting the device 400. The bottom housing 404 can include a mount for the rotation screw 410 (FIG. 4C), which can control the relative angular orientation of the two housing pieces 402, 404. When the screw 410 is rotated by an external tool (e.g. as shown in FIGS. 8A-8I), the screw 410 engages the internal teeth/ridges 414 of the top housing 402 and acts as a wedge to rotate the top housing 402 away from the bottom housing 404. More particularly, the device 400 can include a sloped ridge 414, as exemplary illustrated in FIG. 4C. When the rotating screw 410 advances, the top housing 402 rotates further and further away from the bottom housing 404. The device 400 can include one or more bone cavities in the top housing 402 and bottom housing 404 for bone fusion.

FIGS. 5A-5D illustrate exemplary embodiments of a ZP-EIS device according to embodiment V, which employs an anchor mechanism of expansion.

The top housing 502 and bottom housing 504 can be coupled or attached by one or more pins, such as two pins 512, which allow rotation of the top housing 502 and bottom housing 504 relative to each other about the axis of the pins 512. The top housing 502 and/or the bottom housing 504 can include indentations 506 on their lateral sides close to the top of the device 500 to mate with the prongs of a tool or universal tool (e.g. see FIGS. 8A-8I) to assist in grasping, inserting and impacting the device 500. The bottom housing 504 can include, for example, a mount for the lead (rotation) screw 510, which can control the relative angular orientation of the two housing pieces 502, 504. The lead (rotation) screw 510 can be secured with one or more retaining rings, such as two retaining rings 518. When the screw 510 is rotated by an external tool (not illustrated)(e.g., such as the tool shown in FIGS. 8A-8I), the screw 510 causes lateral motion of a translation nut 516, which is attached to two linkage bars 514 to a second nut 516 fixed to the bottom housing. A plurality of pins, such as six pins 512, can secure the linkage bars or arms 514 to each other and to translation nuts 516. When the translation nuts 516 move, the linkage bars or arms 514 extend outside of the bottom housing 504, pushing against the top housing 502. Alternatively, in other embodiments, the linkage bars or arms 514 can be replaced by a solid material such as spring steel which can bend to produce the same effect. The device 500 can include one or more bone cavities that can be incorporated into the top housing 502 and the bottom housing 504 for bone fusion.

FIGS. 6A-6D illustrate exemplary embodiments of a ZP-EIS device 600 according to embodiment VI which employs a modified wedge expansion mechanism.

The device 600 includes a top housing 602 and a bottom housing 604 that can be attached or coupled by one or more pins, such as two pins 612, which allow rotation of the top housing 602 and the bottom housing 604 relative to each other about the axis of the pins 612. The top housing 602 and/or the bottom housing 604 can include indentations 606 on their lateral sides close to the top of the device 600 to mate with the prongs of a tool, such as prongs 806 of the universal tool shown in FIGS. 8A-8I, to assist in grasping, inserting and impacting the device 600. The bottom housing 604 can include a mount for the lead (rotation) screw 610, which can control the relative angular orientation of the two housing pieces 602, 604. The lead (rotation) screw 610 can be secured with one or more retaining rings, such as two retaining rings 618. When the screw 610 is rotated by an external tool (e.g., the tool shown in FIGS. 8A-8I), the screw 610 causes lateral motion of a wedge-shaped translation nut 616. The nut 616 engages an inner tapered surface of the top housing 602 and forces the top housing piece 602 to rotate away from the bottom housing 604. The device 600 can include one or more bone cavities 608 incorporated into the top housing 602 and/or bottom housing 604 for bone fusion.

FIGS. 7A-7D illustrate exemplary embodiments of a ZP-EIS device 700 according to embodiment VII, which employs a worm drive (gear) mechanism.

According to the invention, the device 700 includes a worm drive design that allows a user to rotate a worm gear/drive 712 with an external tool (FIG. 8) to control the translation of the top housing 702 relative to the bottom housing 704a, 704b. The worm gear drive 712 engages a spur gear mount 714 which has internal threading for engaging a corresponding part, such as a threaded stud of bolt 720, to couple the spur gear mount 714 to the top housing 702. The top housing 702 can include a plurality of pins, such as four pins 712, which extend into the bottom housing 704a, 704b. These pins 712 prevent the top housing 702 from rotating with the spur gear 714, and constrain the spur gear 714 to translate linearly. The bottom housing 704 can include two halves 704a, 704b to secure the worm drive 710 and spur mount 714 in place. A worm retaining ring and a spur retaining ring 716 also can be used to secure the worm gear drive 710 and the spur gear mount 714. The device 700 can include one or more bone cavities 708 that are incorporated into the top housing 702 and/or bottom housing 704a, 704b for bone fusion. The top housing 702 and/or bottom housing 704a, 704b can include one or more indentations 706 on its lateral sides close to the top of the device 700 to mate with prongs of a tool, such as prongs 806 of the universal tool 800 in FIGS. 8A-8I, to assist in grasping, inserting and impacting the device 700.

Figure 8A:
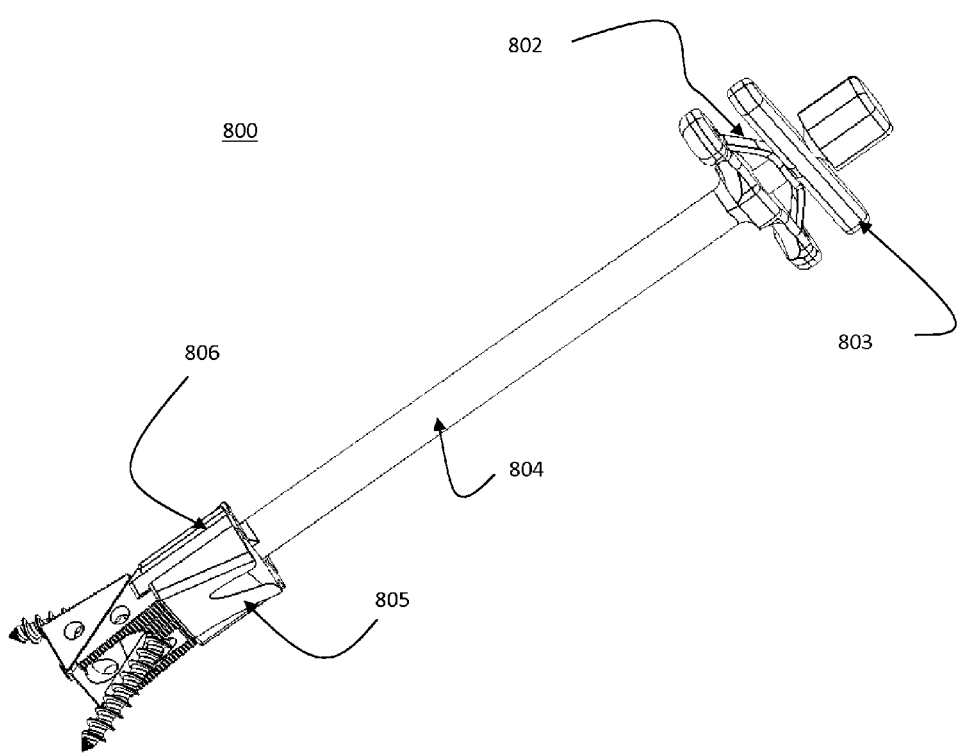
FIG. 8A-8C illustrate a positioning tool/screw guide/box expander in oblique perspective (FIG. 8A), lateral (FIG. 8B), and exploded (FIG. 8C) views according to an exemplary embodiment, which is shown coupled to the exemplary non-tapered sliding base ZP-EIS device illustrated in FIGS. 1A-1B.
Figure 8B:
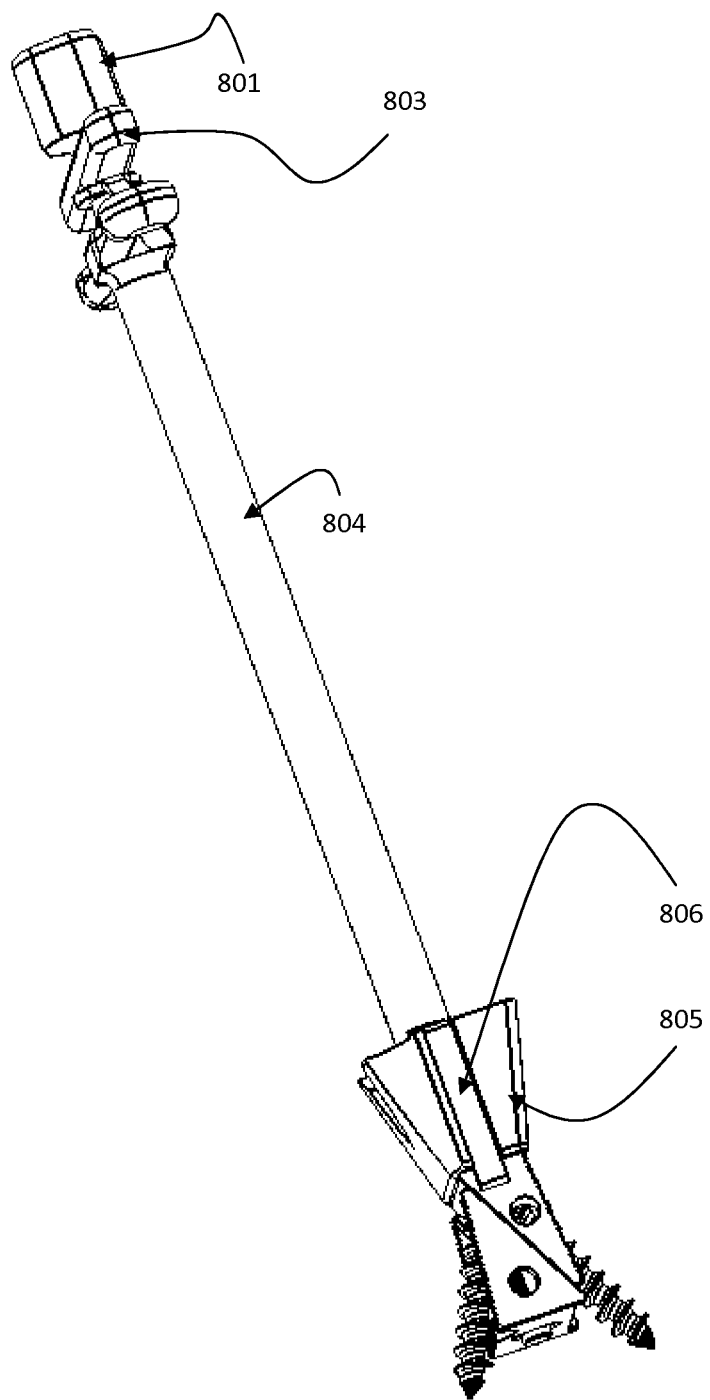
Figure 8C:
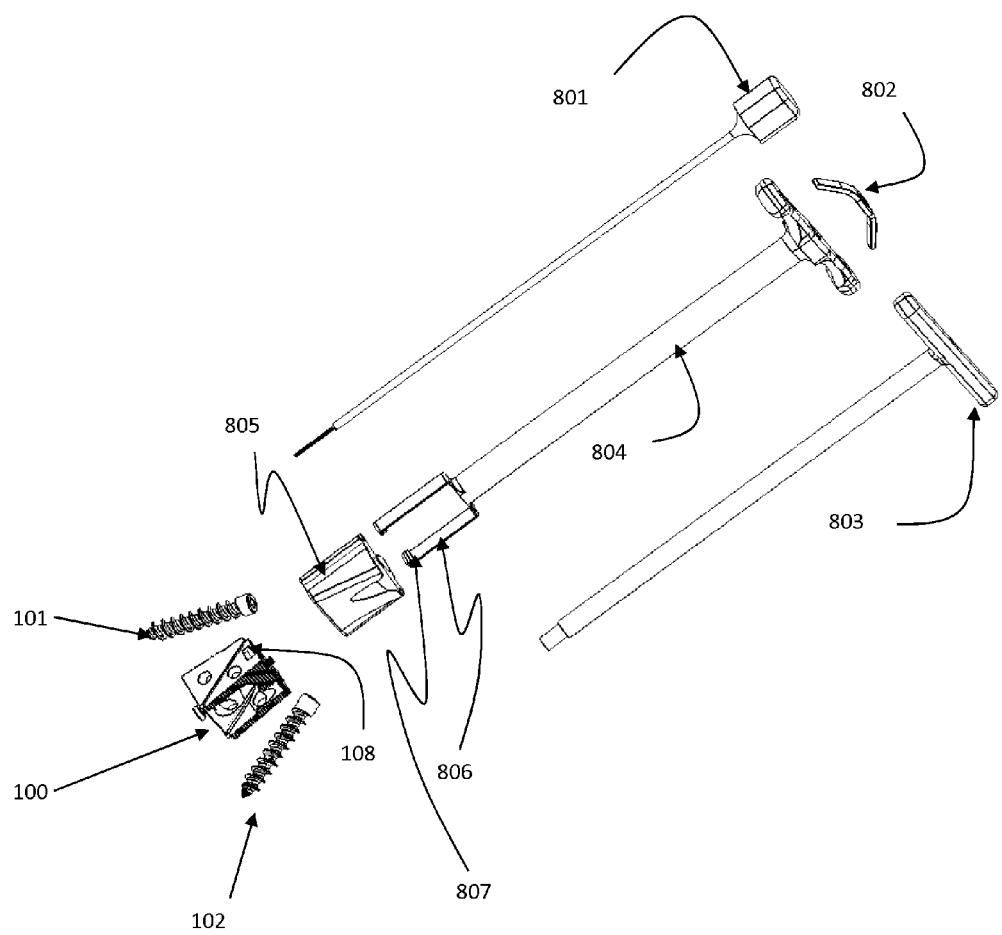

FIGS. 8A-8C illustrate three-dimensional views of exemplary embodiments of the external drill/screw guide-box expander universal tool 800 which can be used to assist in both screw trajectory and box expansion of an expandable device, such as the exemplary embodiments of devices illustrated in embodiments I and II, and for device expansion of the devices illustrated in embodiments III-VII. The same universal tool 800 can be utilized for all the exemplary embodiments illustrated in embodiments I-VII. In some embodiments, the external drill/screw guide 850 may not be needed or used for embodiments II-VII. The prongs 806 can be inserted into the indentations (e.g., 202, 306, 406, 506, 606, 706) of the sides of the devices (e.g., 100, 200, 300, 400, 500, 600, 700) according to one or all of the exemplary embodiments illustrated in embodiments I-VII, and implant the device into the intervertebral space. Once implanted and impacted, an Allen key (e.g., as shown in FIG. 8) can be used to expand the device (e.g., 100, 200, 300, 400, 500, 600, 700) by turning the adjustment (rotation) screw (e.g., 105, 220, 314, 410, 510, 610, 710).

The exemplary tool can include, among other things, an Allen key 801, a spring 802, a handle 803, a griper 804 and a screw guide 805. The Allen key 801, when inserted in the insertion 814 and turned, can turn the rotation screws (e.g., 105, 220, 314, 410, 510, 610, 710) of one or all of the exemplary embodiments I-VII. The griper 804 includes griper prongs 806, which insert into grooves 509 of the screw guide 805 and the screw box indentations (e.g., 202) in the exemplary embodiment illustrated in embodiment I (as shown in FIGS. 8A-8D), as well as in similar indentations (e.g., 306, 406, 506, 606, 706) of devices (e.g., 100, 200, 300, 400, 500, 600, 700) illustrated in embodiments II-VII (not shown).

As shown in FIG. 8C, each longitudinal end of the screw box 100 can include a slot or indentation 108 formed adjacent to an edge of an upper surface of the screw box 100 for engaging a protuberant extension of a tool, such as the protuberant extension 807 of the tool 800.

FIG. 8D illustrates a superior oblique view of the screw guide 805 demonstrating insertions 809 for griper prong 806, built-in trajectory guides 811, 812 for insertion of screws 101 and 102, and the Allen key 801. This exemplary embodiment can be limited, for example, to use with the devices of embodiments I and II, which includes BDFT screws.

Figure 8E:
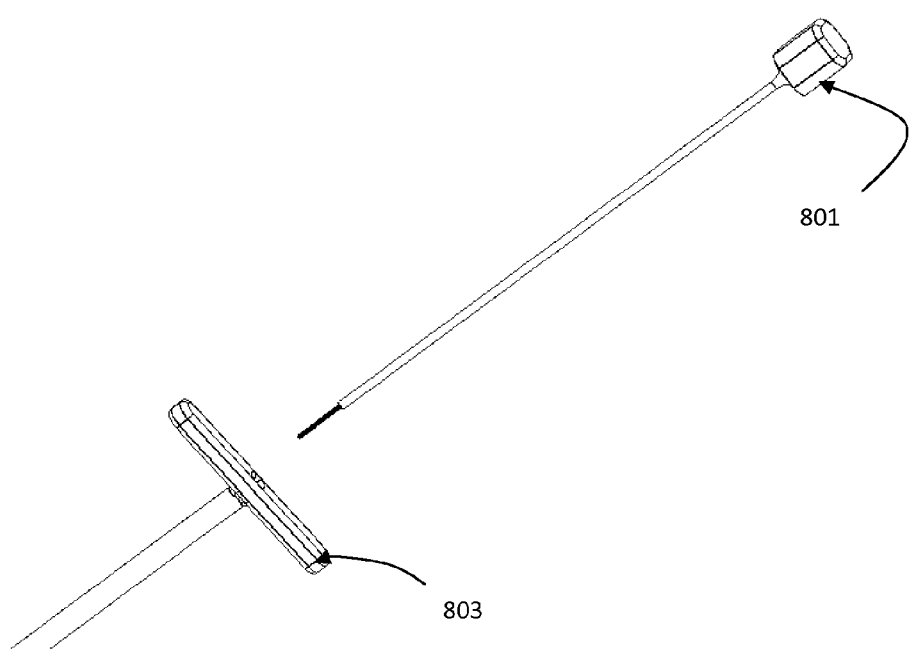
FIGS. 8E-8G illustrate sequential steps (I-III: Step I (FIG. 8E), step II (FIG. 8F), and step III (FIG. 8G)) of the positioning tool/screw guide/box expander assembly according to an exemplary embodiment.
Figure 8F:
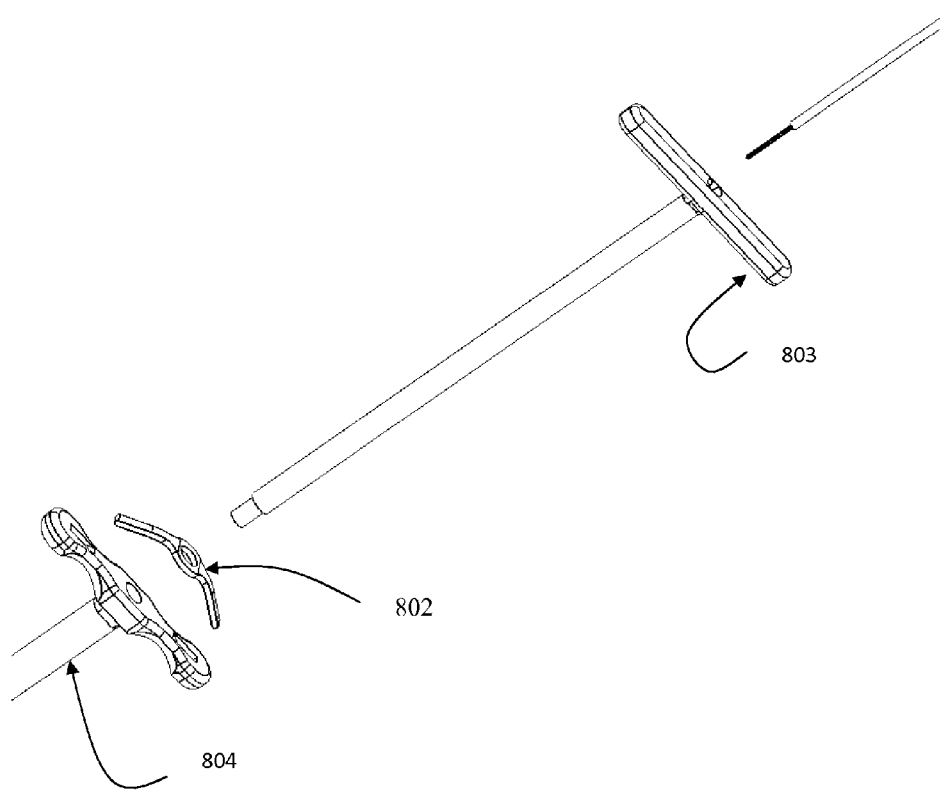
Figure 8G:
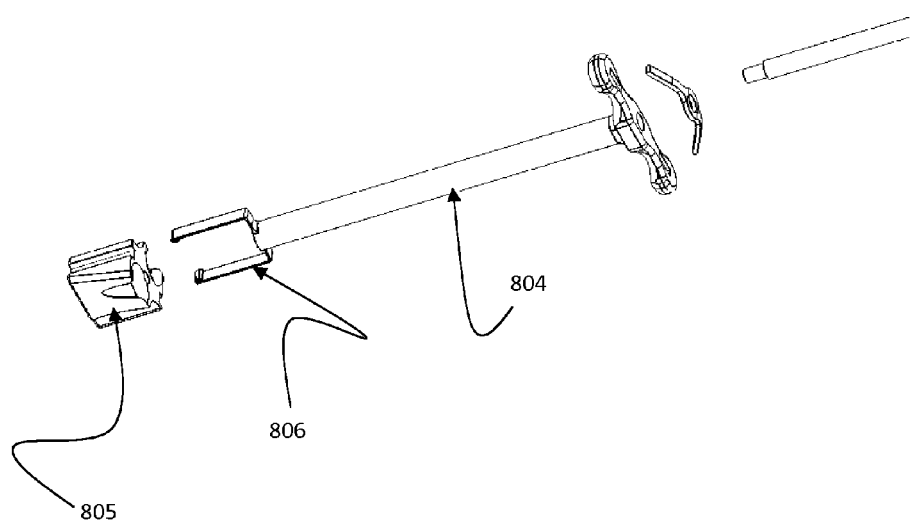

FIGS. 8E-8G illustrate three-dimensional views of the sequential steps necessary for the external guide assembly. FIG. 8E illustrates the insertion of the Allen key 801 into the handle 803. FIG. 5F illustrates the insertion of the handle 803 through the spring 802 and griper 804. FIG. 8G illustrates insertion of the griper 804 into the screw guide 805. The griper prongs 806 can include medially oriented male protuberant extensions 807 that engage the slot or indentation of a device, such as indentation 108 of device 100, thereby perfectly aligning the prongs 805 of the tool 800 with the device (e.g., 100, 200, 300, 400, 500, 600, 700). This exemplary embodiment can be limited, for example, to use with the devices of embodiments I and II.

Figure 8H:
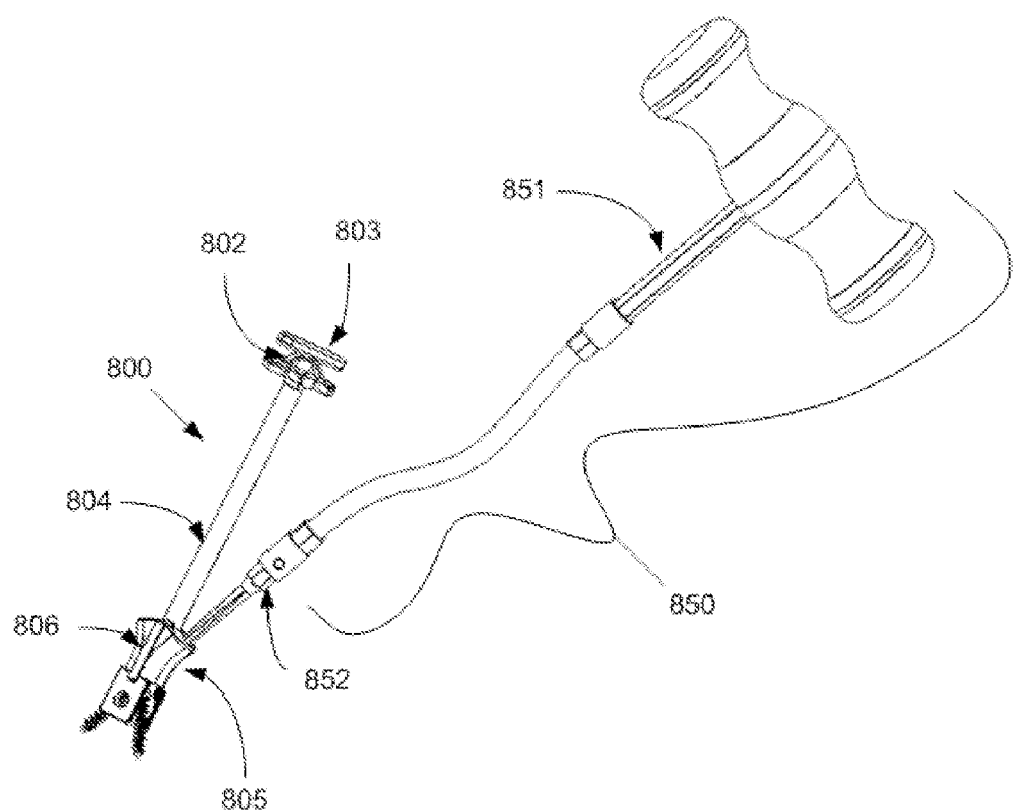
FIGS. 8H-8I illustrate three-dimensional views of positioning tools, according to exemplary embodiments, for impaction and placement of two transvertebral screws, for example, of the exemplary embodiments illustrated in FIGS. 1A-1B and 2A-2D.
Figure 8I:
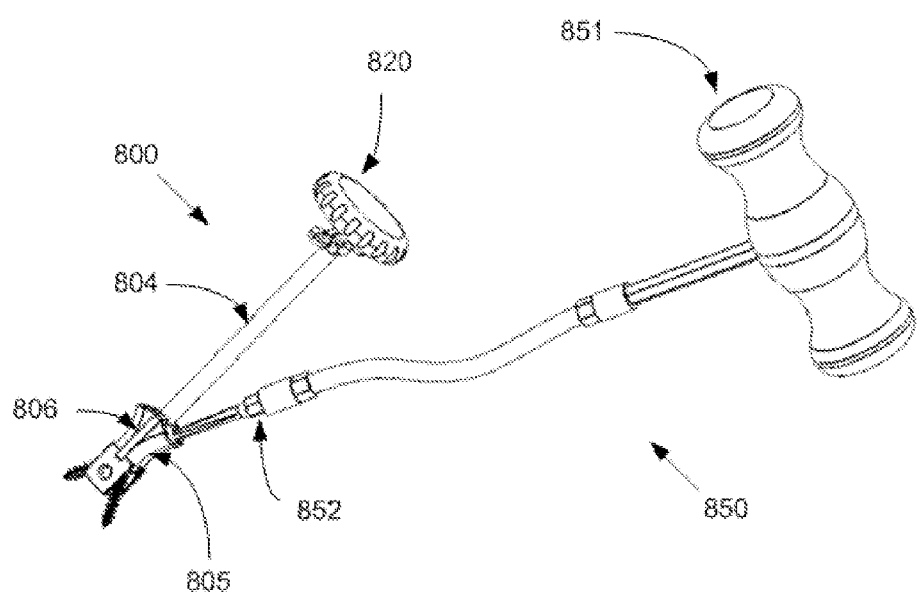

FIG. 8H illustrates a three-dimensional view of another exemplary embodiment of a positioning tool 800 for impaction and placement of two transvertebral screws 201, 202 for example, for use with the exemplary embodiments I and II.

With reference again to FIGS. 8A-8K, the screw guide 805 can include insertions 809 for receiving the griper prong 806, built-in trajectory guides 811, 812 for insertion of screws 101 and 102, and the Allen key 801.

The driver assembly 850 can include a screw driver 851, a flexible shaft 852 and a square recess bit 853. This exemplary device can facilitate turning the screws 101, 102 into the bone. The flexible shaft 852 can facilitate the avoidance of spinous processes which might hinder the screw driving if the shaft 852 were straight. The positioning tool 800 can have a rectangular handle, as shown for example in Embodiment I, or a circular handle, as exemplary shown in Embodiment II. This exemplary embodiment can serve to position a screw box within the intervertebral space, and screws 101, 102 within the screw box or device. Once positioned, the screw box or device (e.g., 100, 200, 300, 400, 500, 600, 700) can be impacted by tapping the handle 803 with a mallet (not shown). The griper handle 803 inserts into the screw guide and the screw box or device (e.g., 100, 200, 300, 400, 500, 600, 700), which maintains alignment.

2. The Surgical Method

Exemplary embodiments of a surgical method for utilizing the exemplary devices described herein, will now be described. The procedures can be performed open, microscopic, closed tubular or endoscopic. Fluoroscopic guidance can be used with any of these procedures.

Figure 8J:
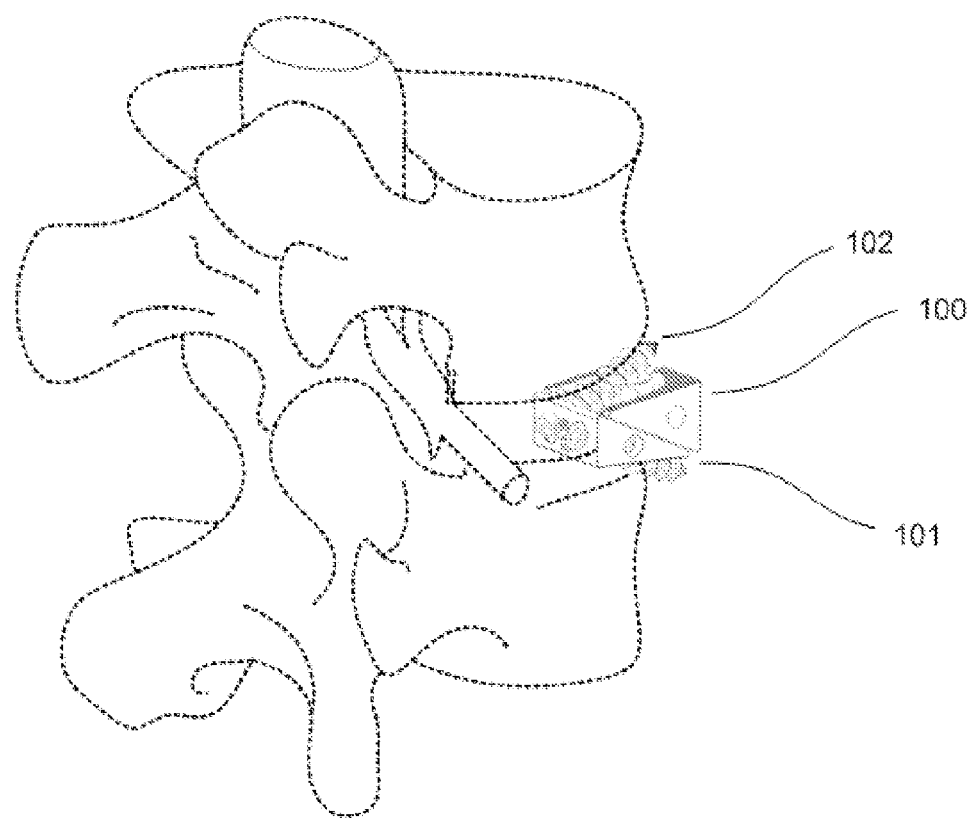
FIGS. 8J-8K illustrate the insertion of expandable Lumbar bi-directional screw box with two BDFT screws into the Lumbar spine in oblique (FIG. 8J) and lateral (FIG. 8K) views.
Figure 8K:
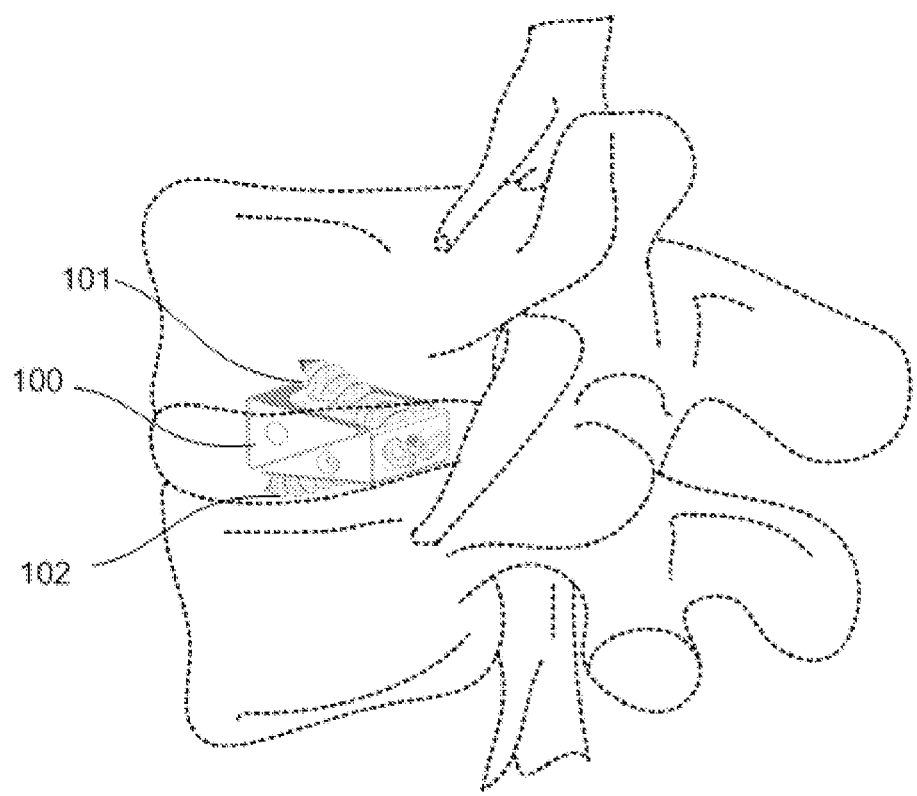

An exemplary embodiment of a ZP-EIS device, as illustrated in embodiments (I-VII), can be inserted into the intervertebral space (for example as shown in FIGS. 8J and 8K) after an adequate discectomy is performed in any disc space throughout the entire spine upon their exposure anteriorly, anterio-laterally, laterally, far laterally or posteriorly.

For exemplary embodiments I-II of the ZP-EIS devices can be inserted into the disc space by a tool or universal tool, such as the universal tool 800 in FIGS. 8A-8I. In operation, the grab prongs of tool 800 can attach to the insets or indentations (e.g., 202, 306, 406, 506, 606, 706) on the side of the devices. Once in the disc space, the rotation screw (e.g., 105, 220, 314, 410, 510, 610, 710) of each embodiment is turned by rotating the Allen key 801 of the tool 800 to expand the device (e.g., 100, 200, 300, 400, 500, 600, 700) to the desirable disc height achieving the desirable intervertebral distraction deemed necessary for the individual patient and disc space. Once this is achieved, BDFT screws 101, 102 are inserted and screwed into the vertebral body above and below securing the device (e.g., 100, 200, 300, 400, 500, 600, 700) to the vertebral bodies with screws 101, 102. Prior to implantation of the device (e.g., 100, 200, 300, 400, 500, 600, 700), the bone cavities of each device can be filled with any type of bone fusion material.

For the exemplary embodiments III-VII, the ZP-EIS device (e.g., 100, 200, 300, 400, 500, 600, 700) can be inserted into the disc space by the same universal tool, such as tool 800. The grabs prongs 806 of the tool 800 attach to the insets or indentations (e.g., 202, 306, 406, 506, 606, 706) on the side of the devices (e.g., 100, 200, 300, 400, 500, 600, 700) on the side of the devices (e.g., 100, 200, 300, 400, 500, 600, 700). Once in the disc space, the rotation screw (e.g., 105, 220, 314, 410, 510, 610, 710) is turned by rotating the Allen key 801 of the tool 800 expanding the device (e.g., 100, 200, 300, 400, 500, 600, 700) to the desirable disc height achieving the desirable intervertebral distraction deemed necessary for the individual patient and disc space. Prior to implantation of the device (e.g., 100, 200, 300, 400, 500, 600, 700) the bone cavities of each device (e.g., 100, 200, 300, 400, 500, 600, 700) can be filled with any type of bone fusion material.

The exemplary embodiments of the present invention may provide effective and safe techniques that overcome the problems associated with current transpedicular and/or plated fusion technology employed for many degenerative stable and unstable spine diseases. These exemplary embodiments may replace much pedicle screw-based and plated based instrumentation in many but not all degenerative spine conditions.

The speed and simplicity of the surgical implantation of the exemplary embodiments of the ZP-EIS devices far exceeds that of conventional pedicle screw technology. Furthermore, the exemplary embodiments of zero-profile devices can provide markedly significantly decreased risk of misguided screw placement, and hence decreased risk of neural and vascular injury, and blood loss. The exemplary embodiments can provide decreased recovery and back to work time. The exemplary embodiments of devices may lead to similar if not equal fusion with significantly less morbidity, and hence overall make the exemplary devices a major advance in the evolution of spinal instrumented technology leading to advances in the care of the spinal patient.

According to the exemplary embodiments, such as the embodiments in embodiments I and II, an intervertebral fusion device is provided that uses a threaded rod mechanism located at the peripheral of the box to control expansion of the device. The device can include a cavity within the walls for placement of bone material for fusion.

In another embodiment, an intervertebral fusion device can include a threaded rod which can obstruct (inhibit) expansion of the device when it is not being turned. The threaded rod can be disposed at the front anterior part of the box or device.

In yet another embodiment, an intervertebral fusion device can include a threaded rod, which exerts a clamping force to expand the device until the device properly accommodates the dimensions of the intervertebral disc space and distracts the space based on individual anatomy and surgical judgment. The device can include a cavity for bone in-between the walls of the box.

In another embodiment, an expandable intervertebral fusion device can includes indentations on its sides to accommodate a placement tool.

In another embodiment, an expandable intervertebral fusion device can be adjusted by using a threaded rod as a wedge to pivot components within the device. The threaded rod can be accessible from the front anterior of the box or device.

In another embodiment, an expandable fusion device can include a threaded rod to expand a spacer. The threaded rod can be used as a wedge to mechanically separate the pieces. The threaded rod can be accessible from the front anterior of the box or device.

In another embodiment, an expandable fusion device can include wedge components which translate relative to each other along a contact. The degree of expansion can be determined by an adjustment rod located at the peripheral of the box or device.

In another embodiment, an expandable fusion device includes components which are mechanically linked together. The expansion of the device is controlled by the user via an adjustment rod coupled to a mechanical transmission that causes mechanical components within the device to separate. The threaded rod is accessible from the front anterior of the box or device.

In another embodiment, an expandable fusion device can be provide wherein the position of the device is secured and adjusted by a threaded rod that is mechanically linked to housing pieces. When the threaded rod is rotated, the threaded rod forces the pieces to separate.

In another embodiment, an intervertebral fusion device is provide wherein the two internal screw guides are in the top housing unit.

In another embodiment, an intervertebral fusion expansile device is provided wherein the center of the two internal screw guides could be in quadrants I and III or II and IV.

In another embodiment, an expandable fusion device can be provided that uses a threaded rod (rotation screw) to expand the device using a metal driver as the wedge to mechanically separate the pieces.

In another embodiment, an expandable fusion device can be adjusted by using a threaded rod (rotation screw) as a wedge to offset the opposing cages.

In another embodiment, an expandable intervertebral fusion device can be provided wherein its position is secured and adjusted by a threaded rod (rotation screw) coupled to a nut and passed through the top and bottom housing pieces. As the threaded rod is rotated further into the nut, the pieces separate.

In another embodiment, an expandable intervertebral fusion device can include a tapered edge to allow contoured insertion into the disc space.

In another embodiment, an intervertebral fusion device can be provided wherein the internal screw guides for screw insertion within the device are diagonal to each other within the xyz plane.

In another embodiment, an intervertebral fusion device wherein the internal screw guides can be adjacent and somewhat diagonal to each other within the xyz plane.

In another embodiment, an intervertebral fusion device can be provided wherein the majority each of the 2 screw holes can be in quadrant I and III or II and IV within the xyz plane.

In another embodiment, an intervertebral fusion device can be provided wherein the screw guides can have approximately the same xy coordinates and have different z coordinates or vice versa.

In another embodiment, an intervertebral fusion device can be provided wherein the center of the two internal screw guides could be in quadrants I and III or II and IV within the xyz plane.

In another embodiment, an intervertebral fusion device can be provided wherein one screw guide is in the top housing unit, and another screw guide is in the bottom housing unit.

In another embodiment, an intervertebral fusion device can be provided that uses a threaded rod (rotation screw) to engage a moveable component which engages a linkage to expand the device.

In another embodiment, an intervertebral fusion device can be provided that uses a threaded rod (rotation screw) to engage a wedge which engages its attaching linkages to expand the device.

In another embodiment, an expandable fusion device can be provided that can be adjusted using a threaded rod (rotation screw) coupled to a scissor-jack linkage.

In another embodiment, an expandable fusion device can be held together with fastener (s). These fasteners constrain the box to one degree of freedom. Part of the mechanism contains a mount for the rotation screw, which can control the movement of the pieces. As the screw is turned, it engages the teeth of the mechanism and acts as a wedge to rotate the pieces away from each other.

In another embodiment, an expandable fusion device adjusted by using a threaded rod (rotation screw) can be used as a wedge to offset the opposing cage surfaces.

In another embodiment, an expandable fusion device can be provided that uses a threaded rod (rotation screw) to expand the device using a metal driver as the wedge to mechanically separate the pieces.

In another embodiment, an expandable fusion device can be provided that can be adjusted by a threaded rod (rotation screw) coupled to a nut which translates to deform an elastomeric material used to force the expansion of the device.

In another embodiment, an expandable fusion device can be provided that has a threaded rod (rotation screw) that engages a wedge to control the expansion of the device.

In another embodiment, an expandable fusion device can be provided that can be contained by fasteners and retaining rings.

In another embodiment, an expandable fusion device can be provided that can be adjusted by a threaded rod (rotation screw) coupled to a wedge that can move the opposing cage surfaces.

In another embodiment, an expandable fusion device can be provided that uses a worm drive to turn a gear that acts as a wedge to expand the device.

In another embodiment, an expandable fusion device can be provided that includes fasteners and retaining rings containing and constraining the device pieces.

In another embodiment, an expandable fusion device can be provided that can be adjusted by a worm gear coupled to an internally threaded spur gear which, upon rotation, linearly advances a threaded component.

In another embodiment, a tool includes a handle, a gripper cooperating with the handle and having a plurality of prongs, a screw guide held in place the plurality of prongs, for controlling the direction of self-drilling screws that are screwed into the vertebral bodies, and an Allen key which expands expandable intervertebral devices.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

We claim:

1. An expandible intervertebral fusion device comprising:
a first movable portion;
a second movable portion; and
a mechanism that moves the first movable portion and the second movable portion with respect to each other to expand a dimension of the expandible intervertebral fusion device,
wherein the first movable portion includes:
a top wall, a bottom wall, and two sidewalls defining an open space capable of receiving bone filling for the biological bone fusion; and
an internal screw guide having an entry opening and an exit opening, the entry opening formed only in a top surface of the top wall and the exit opening formed at least partially in a bottom surface of the top wall and at least partially in a side surface of the top wall.

2. The device of claim 1, wherein the first movable portion slides with respect to the second movable portion.

3. The device of claim 1, wherein the first movable portion pivots with respect to the second movable portion.

4. The device of claim 1, wherein the first movable portion translates linearly away from the second movable portion.

5. The device of claim 1, wherein the first movable portion slides at an angle with respect to the second movable portion.

6. The device of claim 1, wherein the mechanism includes a threaded rod mechanism.

7. The device of claim 1, wherein the second movable portion includes an open space capable of receiving bone filling for the biological bone fusion.

8. The device of claim 1, wherein one of the first movable portion and the second movable portion includes an indentation to accommodate a component of a placement tool.

9. The device of claim 1, wherein the first movable portion and the second movable portion can be adjusted by using a threaded rod as a wedge to pivot components within the device.

10. The device of claim 1, wherein the first movable portion and the second movable portion can be adjusted using a wedge device.

11. The device of claim 1, wherein the mechanism separates the first movable portion from the second movable portion.

12. The device of claim 1, wherein the second movable portion includes a second internal screw guide.

13. The device of claim 1, wherein one of the first movable portion and the second movable portion includes a tapered edge to allow contoured insertion into the disc space.

14. The device of claim 1, wherein the first movable portion and the second movable portion can be adjusted using a threaded rod coupled to a scissor-jack linkage.

15. The device of claim 1, wherein the first movable portion and the second movable portion can be held together by fasteners.

16. The device of claim 1, wherein the mechanism includes a worm drive or a worm gear.

17. The device of claim 1, wherein the mechanism includes a worm drive that turns a gear that acts as a wedge to expand the device.

18. The device of claim 1, further comprising fasteners and retaining rings containing and constraining the device pieces.

19. The device of claim 1, wherein the mechanism includes a worm drive to turn a gear that acts as a wedge to expand the device.

20. The device of claim 1, wherein the first movable portion and the second movable portion can be adjusted by a worm gear coupled to an internally threaded spur gear which, upon rotation, linearly advances a threaded component.

21. The device of claim 1, wherein first and second screw members are medially aligned.

22. The device of claim 1, wherein at least one of first and second screw members is laterally aligned.

23. The device of claim 3, wherein both first and second screw members are laterally aligned.

24. The device of claim 1, wherein one of first and second screw members is laterally aligned and an other screw member is medially aligned.

25. The device of claim 1, wherein each of the first movable portion and the second movable portion has a substantially triangularly shape.

26. The device of claim 6, wherein the first movable portion and the second movable portion include a sliding rail and ridged surfaces.

27. The device of claim 7, wherein the first movable portion and the second movable portion include holes for bone grafts.

28. The device of claim 8, wherein an adjuster includes a screw.

29. The device of claim 1, wherein one of the first movable portion and the second movable portion includes a sliding rail, and
wherein the other of the first movable portion and the second movable portion includes a rail insert that engages the sliding rail.

30. The device of claim 1, wherein one of the first movable portion and the second movable portion includes a plurality of sliding rails disposed on a side facing the other of the first movable portion and the second movable portion, and
wherein the other of the first movable portion and the second movable portion includes a plurality of rail inserts that engage the plurality of sliding rails.

31. The device of claim 1, wherein one of the first movable portion and the second movable portion the includes an external surface having a plurality of ridges.

32. The device of claim 1, wherein each of the first movable portion and the second movable portion includes an external surface having a plurality of ridges.

33. The device of claim 1, wherein one of the first movable portion and the second movable portion includes a hole for bone grafts.

34. The device of claim 1, wherein each of the first movable portion and the second movable portion the includes a hole for bone grafts.

35. The device of claim 1, wherein one of the first movable portion and the second movable portion includes a plurality of holes for bone grafts.

36. The device of claim 1, wherein an adjuster includes a screw that engages each of the first movable portion and the second movable portion.

37. The device of claim 12, wherein the second movable portion includes a second top wall, and
wherein the second internal screw guide of the second movable portion has an entry opening and an exit opening, the entry opening formed only in a top surface of the second top wall.

38. The device of claim 37, wherein the exit opening of the second internal screw guide of the second movable portion is formed at least partially in a bottom surface of the second top wall and at least partially in a side surface of the second top wall.

39. The device of claim 1, wherein the mechanism comprises a threaded rotation screw extending between the first movable portion and the second movable portion that moves the first movable portion with respect to the second movable portion in response to rotation of the threaded rotation screw, wherein first and second indentations are defined on outer sides of the two sidewalls, wherein means for facilitating incorporation into and fusion with superior and inferior vertebral bodies is positioned on at least part of the two sidewalls of the first movable portion, and wherein the second movable portion has a second internal screw guide having an entry opening formed only in a top surface of a top wall of the second movable portion and extending in a different direction than that of the internal screw guide such that the internal screw guide and second internal screw guide direct screws into the superior and inferior vertebral bodies.

40. The device of claim 39, wherein the threaded rotation screw is positioned in a circular hole defined in the second movable portion.

41. The device of claim 39, and further comprising means for promoting segmental spinal fusion.

42. A system comprising the device of claim 39, wherein the system further comprises:
a tool comprising:
an elongate shaft;
first and second gripper prongs that are sized and positioned such that the first gripper prong engages the first indentation and the second gripper prong engages the second indentation when the tool engages the device; and
a tool screw guide defining first and second screw trajectory guides, wherein the first screw trajectory guide aligns with the first internal screw guide and guides a direction of insertion of a screw when the tool is engaged with the device, wherein the first and second gripper prongs extend distally past the tool screw guide on opposite sides of the tool screw guide; and a screwdriver sized and configured for driving screws through the first and second internal screw guides while the tool is holding the device between first and second vertebral bodies.

43. The system of claim 42, wherein the first and second screw trajectory guides are defined in opposite sides of the tool screw guide with each of the first and second screw trajectory guides having a partially tubular shape that is curved on one side and open on an opposite side.

44. The device of claim 39, and further comprising means for sliding the first movable portion with respect to the second movable portion when the threaded rotation screw is turned.

45. The device of claim 44, and further comprising means for retaining the threaded rotation screw.

46. The device of claim 39, wherein the device is configured such that rotation of the threaded rotation screw can move a top wall of the second movable portion above the top wall of the first movable portion.

47. An expandible intervertebral fusion device comprising:
a first movable body;
a second movable body; and
means for moving the first movable body with respect to the second movable body to expand a dimension of the expandible intervertebral fusion device,
wherein the first movable body includes:
a top wall, a bottom wall, and two sidewalls defining an open space capable of receiving bone filling for the biological bone fusion; and
an internal screw guide having an entry opening and an exit opening, the entry opening formed only in a top surface of the top wall and the exit opening formed at least partially in a bottom surface of the top wall and at least partially in a side surface of the top wall.

48. An expandible intervertebral fusion device comprising:
a first movable portion;
a second movable portion; and
a mechanism that moves the first movable portion and the second movable portion with respect to each other to expand a dimension of the expandible intervertebral fusion device,
wherein the first movable portion includes a first top wall, a first bottom wall, a first sidewall, and a second sidewall defining a first open space capable of receiving bone filling for the biological bone fusion, wherein the second movable portion includes a second top wall, a second bottom wall, a third sidewall, and a fourth sidewall defining a second open space capable of receiving bone filling for the biological bone fusion,
wherein the first top wall of the first moveable portion and the second top wall of the second moveable portion cooperate to form a top wall of the expandible intervertebral fusion device,
wherein the first movable portion includes a first internal screw guide having an entry opening and an exit opening, the entry opening formed entirely between all edges of a top surface of the first top wall when viewed from a direction perpendicular to a plane of the top surface of the first top wall and the exit opening formed at least partially in a bottom surface of the first top wall and at least partially in a side surface of the first top wall, and
wherein the second movable portion includes a second internal screw guide having an entry opening and an exit opening, the entry opening formed entirely between all edges of a top surface of the second top wall when viewed from a direction perpendicular to a plane of the top surface of the second top wall and the exit opening formed at least partially in a bottom surface of the second top wall and at least partially in a side surface of the second top wall.

49. The device of claim 48, wherein the mechanism comprises a threaded rotation screw extending between the first movable portion and the second movable portion that moves the first movable portion away from the second movable portion in response to rotation of the threaded rotation screw, wherein a circular hole extend into to the top wall of the expandible intervertebral fusion device in a direction substantially normal to the top wall of the expandible intervertebral fusion device and positioned between the first internal screw guide and the second internal screw guide, wherein a first indentation is defined on a first outer side of the first sidewall and a second indentation is defined on a second outer side of the second sidewall and is positioned opposite of the first indentation, and wherein the first open space capable of receiving bone filling extends continuously from an inner surface of the first sidewall to an inner surface of the second sidewall and extends continuously from an inner surface of the top wall to an inner surface of the bottom wall.

50. the device of claim 49, wherein the threaded rotation screw is positioned in the circular hole.

51. The device of claim 48, wherein a circular hole extend into to the top wall of the expandible intervertebral fusion device in a direction substantially normal to the top wall of the expandible intervertebral fusion device and positioned between the first internal screw guide and the second internal screw guide, wherein a first indentation is defined on a first outer side of the first sidewall and a second indentation is defined on a second outer side of the second sidewall and is positioned opposite of the first indentation, and wherein the first open space capable of receiving bone filling extends continuously from an inner surface of the first sidewall to an inner surface of the second sidewall and extends continuously from an inner surface of the top wall to an inner surface of the bottom wall.

52. The device of claim 51, and further comprising means for promoting segmental spinal fusion.

53. The device of claim 51, and further comprising means for facilitating incorporation into and fusion with superior and inferior vertebral bodies.

54. The device of claim 53, wherein the means is positioned at least partially on the first sidewall adjacent the exit opening of the first internal screw guide and on the fourth sidewall adjacent the exit opening of the second internal screw guide.

55. The device of claim 48, wherein a first indentation is defined on a first outer side of the first sidewall and a second indentation is defined on a second outer side of the second sidewall and is positioned opposite of the first indentation, wherein the first open space capable of receiving bone filling extends continuously from an inner surface of the first sidewall to an inner surface of the second sidewall and extends continuously from an inner surface of the top wall to an inner surface of the bottom wall, wherein each of the first and second movable portions comprise means for facilitating incorporation into and fusion with superior and inferior vertebral bodies, and wherein the means is positioned on each of the first top wall, the second top wall, the first bottom wall, the second bottom wall, and the first, second, third and fourth sidewalls, wherein a first portion of the means is positioned on the side surface of the first top wall between the exit opening of the first internal screw guide and the top surface of the first top wall, and wherein a second portion of the means is positioned on the side surface of the second top wall between the exit opening of the second internal screw guide and the top surface of the second top wall.

\* \* \* \* \*

UNITED STATES PATENT AND TRADEMARK OFFICE
CERTIFICATE OF CORRECTION

PATENT NO.        : 9,848,993 B2                          Page 1 of 2
APPLICATION NO.   : 14/063197
DATED             : December 26, 2017
INVENTOR(S)       : Ahmnon D. Moskowitz et al.

It is certified that error appears in the above-identified patent and that said Letters Patent is hereby corrected as shown below:

On the Title Page

Delete item (60) and insert the below:
-- Continuation in-part of application nos. 13/210,150, filed on Aug. 15, 2011, 13/210,157, filed Aug. 15, 2011, 13/210,162, filed Aug. 15, 2011, 13/210,168, filed Aug. 15, 2011, and 13/741,361, filed Jan. 14, 2013. Application No. 13/210,150 is a continuation of 13/084,543, filed Apr. 11, 2011, now Pat. No. 8,353,913, which is a divisional of 11/842,855, filed Aug. 21, 2007, now Pat. No. 7,942,903, and a continuation of 13/108,982, filed May 16, 2011, which is a continuation of 11/842,855, filed Aug. 21, 2007, now Pat. No. 7,942,903, which is a continuation-in-part of 11/536,815, filed Sept. 29, 2006, now U.S. Pat. No. 7,846,188, which is a continuation-in-part of 11/208,644, filed Aug. 23, 2005, now Pat. No. 7,704,279, which claims priority to 60/670,231, filed Aug. 12, 2005.
Application No. 13/210,157 is a continuation of 13/084,543, filed Apr. 11, 2011, now Pat. No. 8,353,913, which is a divisional of 11/842,855, filed Aug. 21, 2007, now Pat. No. 7,942,903, and a continuation of 13/108,982, filed May 16, 2011, which is a continuation of 11/842,855, filed Aug. 21, 2007, now Pat. No. 7,942,903, which is a continuation-in-part of 11/536,815, filed Sept. 29, 2006, now U.S. Pat. No. 7,846,188, which is a continuation-in-part of 11/208,644, filed Aug. 23, 2005, now Pat. No. 7,704,279, which claims priority to 60/670,231, filed Aug. 12, 2005.
Application No. 13/210,162 is a continuation of 13/084,543, filed Apr. 11, 2011, now Pat. No. 8,353,913, which is a divisional of 11/842,855, filed Aug. 21, 2007, now Pat. No. 7,942,903, and a continuation of 13/108,982, filed May 16, 2011, which is a continuation of 11/842,855, filed Aug. 21, 2007, now Pat. No. 7,942,903, which is a continuation-in-part of 11/536,815, filed Sept. 29, 2006, now U.S. Pat. No. 7,846,188, which is a continuation-in-part of 11/208,644, filed Aug. 23, 2005, now Pat. No. 7,704,279, which claims priority to 60/670,231, filed Aug. 12, 2005.
Application No. 13/210,168 is a continuation of 13/084,543, filed Apr. 11, 2011, now Pat. No. 8,353,913, which is a divisional of 11/842,855, filed Aug. 21, 2007, now Pat. No. 7,942,903, and a continuation of 13/108,982, filed May 16, 2011, which is a continuation of 11/842,855, filed Aug. 21, 2007, now Pat. No. 7,942,903, which is a continuation-in-part of 11/536,815, filed Sept. 29, 2006, now U.S. Pat. No. 7,846,188, which is a continuation-in-part of 11/208,644, filed Aug. 23, 2005, now Pat. No. 7,704,279, which claims priority to 60/670,231, filed Aug. 12, 2005.

Signed and Sealed this
Seventeenth Day of April, 2018

Andrei Iancu
*Director of the United States Patent and Trademark Office*

CERTIFICATE OF CORRECTION (continued)
U.S. Pat. No. 9,848,993 B2

Application No. 13/741,361 is a continuation of 13/084,543, filed Apr. 11, 2011, now Pat. No. 8,353,913, which is a divisional of 11/842,855, filed Aug. 21, 2007, now Pat. No. 7,942,903, and a continuation of 13/108,982, filed May 16, 2011, which is a continuation of 11/842,855, filed Aug. 21, 2007, now Pat. No. 7,942,903, which is a continuation-in-part of 11/536,815, filed Sept. 29, 2006, now U.S. Pat. No. 7,846,188, which is a continuation-in-part of 11/208,644, filed Aug. 23, 2005, now Pat. No. 7,704,279, which claims priority to 60/670,231, filed Aug. 12, 2005.
Claims priority to 61/801,783, filed Apr. 12, 2005 and 61/718,707, filed Oct. 25, 2012. --.

In the Claims

Column 16; Line 2: In Claim 31, delete "portion the" and insert -- portion --, therefor.

Column 16; Line 11: In Claim 34, delete "portion the" and insert -- portion --, therefor.

Column 18; Line 26: In Claim 50, delete "the" and insert -- The --, therefor.

UNITED STATES PATENT AND TRADEMARK OFFICE
CERTIFICATE OF CORRECTION

PATENT NO. : 9,848,993 B2
APPLICATION NO. : 14/063197
DATED : December 26, 2017
INVENTOR(S) : Moskowitz et al.

Page 1 of 1

It is certified that error appears in the above-identified patent and that said Letters Patent is hereby corrected as shown below:

On the Title Page

Column 1, Please add the following Inventor in (72):
David Schoon, Rockville, MD (US)

Signed and Sealed this
Twenty-third Day of May, 2023

Katherine Kelly Vidal
Director of the United States Patent and Trademark Office